United States Patent
Akama et al.

(10) Patent No.: US 6,452,014 B1
(45) Date of Patent: Sep. 17, 2002

(54) TELOMERASE INHIBITORS AND METHODS OF THEIR USE

(75) Inventors: Tsutomu Akama, Redwood City; Ryan Holcomb, San Carlos; Richard L. Tolman, Los Altos, all of CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/748,622

(22) Filed: Dec. 22, 2000

(51) Int. Cl.$^7$ ............................................. A01N 43/78
(52) U.S. Cl. ...................... 546/260; 514/394; 548/182; 548/186; 548/189
(58) Field of Search ................... 548/186, 189, 548/182; 514/367, 394

(56) References Cited

U.S. PATENT DOCUMENTS

| | | | |
|---|---|---|---|
| 4,287,200 A | 9/1981 | Kawamatsu et al. | 427/270 |
| 4,340,605 A | 7/1982 | Kawamatsu et al. | 424/263 |
| 4,376,777 A | 3/1983 | Kawamatsu et al. | 424/270 |
| 4,438,141 A | 3/1984 | Kawamatsu et al. | 424/248.51 |
| 4,444,779 A | 4/1984 | Kawamatsu et al. | 424/263 |
| 4,461,902 A | 7/1984 | Kawamatsu et al. | 548/183 |
| 4,486,594 A | 12/1984 | Kawamatsu et al. | 548/183 |
| 4,572,912 A | 2/1986 | Yoshioka et al. | 514/369 |
| 4,582,839 A | 4/1986 | Meguro et al. | 514/342 |
| 4,687,777 A | 8/1987 | Meguro et al. | 514/342 |
| 4,703,052 A | 10/1987 | Eggler et al. | 514/337 |
| 4,725,610 A | 2/1988 | Meguro et al. | 514/369 |
| 4,738,972 A | 4/1988 | Eggler et al. | 514/314 |
| 4,775,687 A | 10/1988 | Meguro et al. | 514/369 |
| 4,791,125 A | 12/1988 | Clark | 514/369 |
| 4,812,570 A | 3/1989 | Meguro et al. | 546/280 |
| 4,873,255 A | 10/1989 | Yoshioka et al. | 514/369 |
| 4,897,393 A | 1/1990 | Iijima et al. | 514/233.8 |
| 4,897,405 A | 1/1990 | Alessi et al. | 514/360 |
| 4,918,091 A | 4/1990 | Cantello et al. | 514/369 |
| 4,948,900 A | 8/1990 | Iijima et al. | 514/183 |
| 5,002,953 A | 3/1991 | Hindley et al. | 514/275 |
| 5,023,085 A | 6/1991 | Francoeur et al. | 424/449 |
| 5,053,420 A | 10/1991 | Pershadsingh et al. | 514/369 |
| 5,061,717 A | 10/1991 | Clark et al. | 514/342 |
| 5,120,754 A | 6/1992 | Clark et al. | 514/369 |
| 5,132,317 A | 7/1992 | Cantello et al. | 514/369 |
| 5,143,928 A | 9/1992 | Cetenko et al. | 514/369 |
| 5,143,929 A | 9/1992 | Belliotti | 514/364 |
| 5,194,443 A | 3/1993 | Hindley et al. | 514/367 |
| 5,223,522 A | 6/1993 | Clark et al. | 514/369 |
| 5,232,925 A | 8/1993 | Hindley | 514/272 |
| 5,252,735 A | 10/1993 | Morris | 544/121 |
| 5,260,445 A | 11/1993 | Hindley | 548/183 |
| 5,266,582 A | * 11/1993 | deNanteuil | |
| 5,296,605 A | * 3/1994 | deNanteuil | |
| 5,330,999 A | * 7/1994 | de Nanteuil | |
| 5,814,647 A | 9/1998 | Urban et al. | 514/369 |
| 5,824,694 A | 10/1998 | Kurtz et al. | 514/369 |
| 5,874,454 A | 2/1999 | Antonucci et al. | 514/369 |
| 5,886,014 A | * 3/1999 | Fujita | |
| 6,159,997 A | * 12/2000 | Tsujita | |

FOREIGN PATENT DOCUMENTS

| | | |
|---|---|---|
| EP | 0155 845 A1 | 9/1985 |
| EP | 0155 848 A2 | 9/1985 |
| EP | 0155 848 B1 | 9/1985 |
| EP | 0193 256 A1 | 9/1986 |
| EP | 0193 256 B1 | 9/1986 |
| EP | 283035 | * 9/1988 |
| EP | 0295 828 A1 | 12/1988 |
| EP | 0332 332 B1 | 9/1989 |
| EP | 0343643 B1 | 11/1989 |
| EP | 0343 643 A2 | 11/1989 |
| EP | 0677 517 A1 | 10/1995 |
| EP | 745600 | * 12/1996 |
| EP | 796618 | * 9/1997 |
| JP | 02167224 | * 6/1990 |
| JP | 02167225 | * 6/1990 |
| JP | 09165371 | * 6/1997 |
| JP | 10195057 | * 7/1998 |
| WO | WO 89/08651 | 9/1989 |
| WO | WO 91/07107 | 5/1991 |
| WO | WO 92/02520 | 2/1992 |
| WO | WO 94/01433 | 1/1994 |
| WO | 9918081 | * 4/1999 |
| WO | 9930739 | * 6/1999 |
| WO | 9959586 | * 11/1999 |

OTHER PUBLICATIONS

CA 133:261086, abstract of Oguchi, J Med Chem, 2000, 43(16), 3052–3066.*

* cited by examiner

*Primary Examiner*—D. Margaret Seaman
(74) *Attorney, Agent, or Firm*—David J. Earp; J. Michael Schiff

(57) ABSTRACT

Thiazolidinedione compounds, compositions, and methods of inhibiting telomerase activity in vitro and treatment of telomerase mediated conditions or diseases ex vivo and in vivo are provided. The methods, compounds and compositions of the invention may be employed alone, or in combination with other pharmacologically active agents in the treatment of conditions or diseases mediated by telomerase activity, such as in the treatment of cancer. Also disclosed are methods for assaying or screening for inhibitors of telomerase activity.

21 Claims, No Drawings

TELOMERASE INHIBITORS AND METHODS OF THEIR USE

FIELD OF THE INVENTION

The present invention relates to thiazolidinone compounds that inhibit telomerase activity, to pharmaceutical compositions containing the compounds and to the use of the compounds and compositions, alone or in combination with other pharmaceutically active agents, in the treatment of telomerase-mediated conditions or diseases, such as cancer.

BACKGROUND OF THE INVENTION

Telomerase catalyzes the synthesis of telomeres. Telomeres are characteristic tandem repeats (TTAGGG in mammals) found at the ends of most eukaryotic chromosomes, that may be 15–25 kilobases long in human germline cells. With each cell division, about 60–100 bases are lost from the ends of the chromosomes, and as the telomeres shorten, cells eventually reach crisis and apotosis is triggered. See Harley et al., (1991) Mutation Res. 256: 271–282. Telomerase acts to maintain the telomere length just above the crisis level, and are thus responsible for chromosome stability and are involved in the regulation of the cell cycle.

Telomerase is a ribonucleoprotein reverse transcriptase that contains its own RNA template for the synthesis of telomeric DNA. See Blackburn, 1992, Annu. Rev. Biochem., 61:113–129. Telomerase is present in stem and germline cells of normal tissues, and at much higher levels in over 85% of tumors (Kim et al., 1994, Science, 266:2011–2014). Thus, drugs targeted towards telomerase potentially will have a high selectivity for tumor over healthy tissues. Consequently, telomerase inhibition has been proposed as a new approach to cancer therapy.

The inhibition of telomerase activity by antisense strategies directed towards the telomerase RNA component, for example peptide nucleic acids (Norton et al., (1996) Nature Biotech. 14: 615–619) and phosphorothioate oligonucleotides has been reported. Since telomerase is a reverse transcriptase, the use of inhibitors of reverse transcriptases, such as AZT, and other nucleosides has also been reported. Telomerase inhibition by cisplatin, possibly due to crosslinking of the telomeric repeat sequences, is also known (Burger et al., (1997) Eur. J. Cancer 33: 638–644).

We are interested in inhibitors of telomerase that are small molecules, such as thiazolidinediones (see U.S. Ser. No. 09/608,636). Thiazolidinediones comprise a group of structurally related antidiabetic compounds that increases the insulin sensitivity of target tissues (skeletal muscle, liver, adipose) in insulin resistant animals. In addition to these effects on hyperglycemia, thiazolidinediones also reduce lipid and insulin levels in animal models of NIDDM. Recently, the thiazolidinedione troglitazone was shown to have these same beneficial effects in human patients suffering from impaired glucose tolerance, a metabolic condition that precedes the development of NIDDM, as in patients suffering from NIDDM (Nolan et al., (1994) N. Eng. J. Med. 331, 1188–1193). While their mechanism of action remains unclear, it is known that the thiazolidinediones do not cause increases in insulin secretion or in the number or affinity of insulin receptor binding sites, suggesting that thiazolidinediones amplify post-receptor events in the insulin signaling (Colca, J. R., and Morton, D. R. (1990) in New Antidiabetic Drugs (C. J. Bailey and P. R. Flatt, eds.). Smith-Gordon, New York, 255–261; Chang et al. (1983) Diabetes 32, 839–845).

Thiazolidinediones have been found to be efficacious inducers of differentiation in cultured pre-adipocyte cell lines (Hiragun et al. (1988) J. Cell Physiol. 134, 124–130; Sparks et al. (1991) J. Cell. Physiol. 146, 101–109; Kleitzien et al. (1992) Mol. Pharmacol. 41, 393–398). Additionally, thiazolidinediones have been implicated in appetite regulation disorders (see WO 94/25026 A1), and in increase of bone marrow fat content. In addition, thiazolidinedione compounds have been suggested for use in the treatment of psoriasis (U.S. Pat. No. 5,824,694) and climacteric symptoms and mesenchymal tumors (U.S. Pat. No. 5,814,647).

The identification of compounds that inhibit telomerase activity provides important benefits to efforts at treating human disease. Compounds that inhibit telomerase activity can be used to treat telomerase-mediated disorders, such as cancer, since cancer cells express telomerase activity and normal human somatic cells do not possess telomerase activity at biologically relevant levels (i.e., at levels sufficient to maintain telomere length over many cell divisions). Unfortunately, few such compounds, especially compounds with high potency or activity and compounds that are orally bioavailable, have been identified and characterized. Hence, there remains a need for compounds that act as telomerase inhibitors that have relatively high potency or activity and that are orally bioavailable, and for compositions and methods for treating cancer and other diseases in which telomerase activity is present abnormally. The present invention meets these and other needs.

SUMMARY OF THE INVENTION

The present invention provides methods, compounds and compositions that are specific and effective for treating telomerase-mediated disorders, such as malignant conditions by targeting cells having telomerase activity. The methods, compounds, and compositions of the invention can be applied to a wide variety of malignant cell types and avoid the problems inherent in current cancer treatment modalities which are non-specific and excessively toxic.

In a first aspect, the present invention is based on the finding that thiazolidinone compounds are effective in the inhibition of telomerase enzyme activity, in vitro, ex vivo and in vivo. Thus, in certain aspects, the present invention provides methods of inhibiting telomerase by contacting telomerase with the compounds described herein. In particular embodiments, the telomerase to be inhibited is a mammalian telomerase, such as a human telomerase. A related aspect of the present invention is the discovery that thiazolidinone compounds inhibit the proliferation of cells that have telomerase activitiy, such as many cancer cells. Thus, this aspect of the present invention provides methods of inhibiting telomerase activity in a patient, preferably a mammal, suffering from a telomerase-mediated condition or disease, comprising administering to the patient a therapeutically effective. amount of a telomerase inhibiting thiazolidinone compound, or a pharmaceutically acceptable salt thereof.

In another aspect, the present invention provides compounds having the formula:

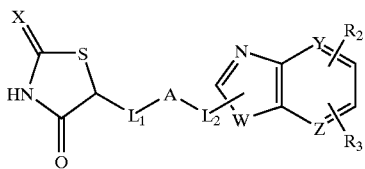

or their pharmaceutically acceptable salts, wherein X is O or S; $L_1$ is a direct bond, —$CHR_1$—, or =$CR_1$—, wherein $R_1$ is H or alkyl; $L_2$ is a direct bond or a linking group having from 1 to 3 atoms independently selected from unsubstituted or substituted carbon, N, O or S; A is aryl or heteroaryl; W is selected from the group consisting of O, $NR_5$, and S, wherein $R_5$ is selected from the group consisting of H, alkyl, aryl, and aralkyl; Y and Z are independently selected to be C or N; and $R_2$ and $R_3$ are independently selected from the group consisting of hydrogen, hydroxyl, halogen, alkyl, aryl, alkoxyl, cyano, nitro, alkylthio, arylthio, aralkyl, and heteroaryl. The compounds find use in methods and compositions for inhibiting a telomerase enzyme, where the telomerase enzyme is contacted with a compound or a composition containing the compound of the invention.

In another aspect, the present invention provides compounds, or their pharmaceutically acceptable salts, having the formula:

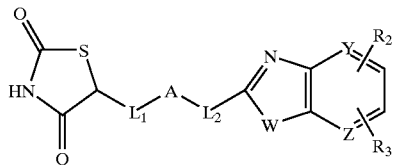

wherein $L_1$ is a direct bond, —$CHR_1$—, or =$CR_1$—, wherein $R_1$ is H or alkyl; A is aryl or heteroaryl; $L_2$ is a direct bond or a linking group having from 1 to 3 atoms independently selected from unsubstituted or substituted carbon, N, O or S; W is selected from the group consisting of O, $NR_5$, and S, wherein $R_5$ is selected from the group consisting of H, alkyl, aryl, and aralkyl; Y and Z are independently selected to be C or N; and $R_2$ and $R_3$ are independently selected from the group consisting of hydrogen, hydroxyl, halogen, alkyl, aryl, alkoxyl, cyano, nitro, alkylthio, arylthio, aralkyl, and heteroaryl.

In another aspect, the present invention provides a compound of formula:

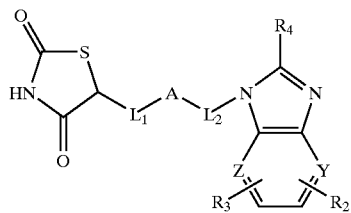

or their pharmaceutically acceptable salts, wherein $L_1$ is a direct bond, —$CHR_1$—, or =$CR_1$—, wherein $R_1$ is H or alkyl; A is aryl or heteroaryl; $L_2$ is a direct bond or a linking group having from 1 to 3 atoms independently selected from unsubstituted or substituted carbon, N, O or S Y and Z are independently selected to be C or N; and $R_2$, $R_3$ and $R_4$ are independently selected from the group consisting of hydrogen, hydroxyl, halogen, alkyl, aryl, alkoxyl, cyano, nitro, alkylthio, arylthio, aralkyl, and heteroaryl.

The new compounds of the invention have many valuable uses as inhibitors of deleterious telomerase activity, such as, for example, in the treatment of cancer in mammals, such as humans. The pharmaceutical compositions of this invention can be employed in treatment regimens in which cancer cells are killed, in vivo, or can be used to kill cancer cells ex vivo. Thus, this invention provides therapeutic compounds and compositions for treating cancer, and methods for treating cancer and other telomerase-mediated conditions or diseases in humans and other mammals (e.g., cows, horses, sheep, steer, pigs and animals of veterinary interest such as cats and dogs).

DETAILED DESCRIPTION

I. Definitions

Unless otherwise defined below, the terms used herein have their normally accepted scientific meanings. Definition of standard chemistry terms may be found in reference works, including Carey and Sundberg (1992) "Advanced Organic Chemistry $3^{rd}$ Ed." Vols. A and B, Plenum Press, New York.

The term "thiazolidinone" or "thiazolidinone derivative" as used herein refers to compounds of the general formula:

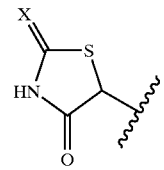

wherein X is O or S. When X is O, the derivatives are thiazolidinedione derivatives. When X is S, the derivatives are the thiazolidinonethione derivatives also known as rhodanines.

The term "alkyl" as used herein refers to a straight, branched, or cyclic hydrocarbon chain fragment or radical containing between about one and about twenty carbon atoms, more preferably between about one and about ten carbon atoms (e.g., methyl, ethyl, n-propyl, isopropyl, cyclopropyl, n-butyl, iso-butyl, tert-butyl, cyclobutyl, adamantyl, noradamantyl and the like). Straight, branched, or cyclic hydrocarbon chains having eight or fewer carbon atoms will also be referred to herein as "lower alkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like). Alkyl groups containing double bonds such as just described will also be referred to herein as "alkenes". Similarly, alkyl groups having triple bonds will also be referred to herein as "alkynes". However, as used in context with respect to cyclic alkyl groups, the combinations of double and/or triple bonds do not include those bonding arrangements that render the cyclic hydrocarbon chain aromatic.

In addition, the term "alkyl" as used herein further includes one or more substitutions at one or more carbon atoms of the hydrocarbon fragment or radical. Such substitutions include, but are not limited to: aryl; heterocycle; halogen (to form, e.g., trifluoromethyl, —$CF_3$); nitro (—$NO_2$); cyano (—CN); hydroxyl (also referred to herein as "hydroxy"), alkoxyl (also referred herein as alkoxy) or aryloxyl (also referred to herein as "aryloxy")(—OR); thio or mercapto, alkyl- or arylthio (—SR); amino, alkylamino, arylamino, dialkyl- or diarylamino, or arylalkylamino (—NRR'); aminocarbonyl, alkylaminocarbonyl, arylaminocarbonyl, dialkylaminocarbonyl, diarylaminocarbonyl or arylalkylaminocarbonyl (—C(O)NRR'); carboxyl, or alkyl- or aryloxycarbonyl (—C(O)OR); carboxaldehyde, or aryl- or alkylcarbonyl (—C(O)R); iminyl, aryl- or alkyliminyl (—C(=NR)R'); sulfo (—SO$_2$OR); alkyl- or arylsulfonyl (—SO$_2$R); ureido (—HNC(=O)NRR'); or thioureido (—HNC(=S)NRR'); where R and R' independently are hydrogen, aryl or alkyl as defined herein. Substituents including heterocyclic groups (i.e., heterocycle, heteroaryl, and heteroaralkyl) are defined by analogy to the above-described terms. For example, the term "heterocycleoxy" refers to the group —OR, where R is heterocycle as defined below.

The alkyl moiety of "lower alkanoyl", "lower alkoxy", "lower alkanoyloxy", "lower alkylthio", is the same as "alkyl" defined above.

The term "methylene" refers to the group —CH$_2$—.

The term "methine" refers to a methylene group for which one hydrogen atom has been replaced by a substituent as described above. The term "methine" can also refer to a methylene group for which one hydrogen atom is replaced by bond to form an sp$^2$-hybridized carbon center (i.e., >C=O).

The term "halo" or "halogen" as used herein refers to the substituents fluoro, bromo, chloro, and iodo.

The term "carbonyl" as used herein refers to the functional group —C(O)—. However, it will be appreciated that this group may be replaced with well-known groups that have similar electronic and/or steric character, such as thiocarbonyl (—C(S)—); sulfinyl (—S(O)—); sulfonyl (—SO$_2$—), phosphonyl (—PO$_2$—), and methylidene (—C(=C$_2$)—). Other carbonyl equivalents will be familiar to those having skill in the medicinal and organic chemical arts.

The term "aryl" as used herein refers to cyclic aromatic hydrocarbon chains having twenty or fewer carbon atoms, e.g., phenyl, naphthyl, biphenyl and anthracenyl. One or more carbon atoms of the aryl group may also be substituted with, e.g.: alkyl; aryl; heterocycle; formyl; halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; ureido; or thioureido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

The term "aralkyl" as used herein refers to an aryl group that is joined to a parent structure by an alkyl group as described above, e.g., benzyl, α-methylbenzyl, phenethyl, and the like. The aralkyl moiety of "aralkylsulfonyl" aralkyloxy is the same as "aralkyl" defined above.

The aryl moiety of "aroyl", "arylalkenyl", "arylalkenyl", "arylsulfonyl", "arylthio", "aryloxy", "arylalkenylsulfonyl", "arylalkynylsulfonyl" is the same as "aryl" defined above.

The term "heterocycle" as used herein refers to a cyclic alkyl group or aryl group as defined above in which one or more carbon atoms have been replaced by a non-carbon atom, especially nitrogen, oxygen, or sulfur. Non-aromatic heterocycles will also be referred to herein as "cyclic heteroalkyl". Aromatic heterocycles are also referred to herein as "heteroaryl". For example, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridinyl, phenazinyl, phenothiazinyl, phenoxazinyl, purinyl, benzimidazolyl, benzthiazolyl, and benzoxazolyl.

The heteroaryl moiety of "heteroarylalkyl", "heteroarylalkenyl", "heteroarylalkynyl", "heteroarylsulfonyl", "heteroarylalkylsulfonyl", "heteroarylalkenylsulfonyl", "heteroarylalkynylsulfonyl", "heteroaryloxy", "heteroarylalkyloxy" is the same as "heteroaryl" defined above.

The above heterocyclic groups may further include one or more substituents at one or more carbon and/or non-carbon atoms of the heteroaryl group, e.g.: alkyl; aryl; heterocycle; halogen; nitro; cyano; hydroxyl, alkoxyl or aryloxyl; thio or mercapto, alkyl- or arylthio; amino, alkyl-, aryl-, dialkyl-diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; ureido; or thioureido. In addition, two or more alkyl substituents may be combined to form fused heterocycle-alkyl or heterocycle-aryl ring systems. Substituents including heterocyclic groups (e.g., heterocycleoxy, heteroaryloxy, and heteroaralkylthio) are defined by analogy to the above-described terms.

The term "heterocyclealkyl" refers to a heterocycle group that is joined to a parent structure by one or more alkyl groups as described above, e.g., 2-piperidylmethyl, and the like. The term "heteroaralkyl" as used herein refers to a heteroaryl group that is joined to a parent structure by one or more alkyl groups as described above, e.g., 2-thienylmethyl, and the like.

The compounds of the present invention may be used to inhibit or reduce telomerase enzyme activity and/or proliferation of cells having telomerase activity. In these contexts, inhibition and reduction of the enzyme or cell proliferation refers to a lower level of the measured activity relative to a control experiment in which the enzyme or cells are not treated with the test compound. In particular embodiments, the inhibition or reduction in the measured activity is at least a 10% reduction or inhibition. One of skill in the art will appreciate that reduction or inhibition of the measured activity of at least 20%, 50%, 75%, 90% or 100% may be preferred for particular applications.

II. Telomerase Inhibitors

As noted above, the immortalization of cells involves inter alia the activation of telomerase. More specifically, the connection between telomerase activity and the ability of many tumor cell lines, including skin, connective tissue, adipose, breast, lung, stomach, pancreas, ovary, cervix, uterus, kidney, bladder, colon, prostate, central nervous system (CNS), retina and blood tumor cell lines, to remain immortal has been demonstrated by analysis of telomerase activity (Kim et al.). This analysis, supplemented by data that indicates that the shortening of telomere length can provide the signal for replicative senescence in normal cells (see WO 93/23572), demonstrates that inhibition of telomerase activity can be an effective anti-cancer therapy. By "inhibition" is simply meant a reagent, drug or chemical which is able to decrease the activity of the telomerase enzyme in vitro or in vivo. Such inhibitors can be readily identified using standard screening protocols in which a cellular extract or other preparation having telomerase activity is placed in contact with a potential inhibitor, and the level of telomerase activity measured in the presence or absence of the inhibitor, or in the presence of varying amounts of inhibitor. In this way, not only can useful inhibitors be identified, but the optimum level of such an inhibitor can be determined in vitro for further testing in vivo.

In a related aspect, the invention proves a method for inhibiting the ability of a cell to proliferate or replicate. In this method, one or more of the thiazolidinone compounds of the invention, that are capable of inhibiting telomerase enzyme activity, are provided during cell replication. As explained above, telomeres play a critical role in allowing the end of the linear chromosomal DNA to be replicated completely without the loss of terminal bases at the 5'-end of each strand. Immortal cells and rapidly proliferating cells use telomerase to add telomeric DNA repeats to chromosomal ends. Inhibition of telomerase will result in the proliferating cells not being able to add telomeres and they will eventually stop dividing. As will be evident to those of ordinary skill in the art, this method for inhibiting the ability of a cell to proliferate is useful for the treatment of a condition associated with an increased rate of proliferation of a cell, such as in cancer (telomerase-activity in malignant cells), and hematopoiesis (telomerase activity in hematopoietic stem cells), for example.

Thus, in one aspect, the present invention provides compounds and compositions for the prevention or treatment of many types of malignancies. In particular, the compounds of the present invention can provide a highly general method of treating many, if not most, malignancies, as demonstrated by the highly varied human tumor cell lines and tumors having telomerase activity. More importantly, the thiazolidinone compounds of the present invention can be effective in providing treatments that discriminate between malignant and normal cells to a high degree, avoiding many of the deleterious side-effects present with most current chemotherapeutic regimes which rely on agents that kill dividing cells indiscriminately. Representative known thiazolidinedione compounds include the glitazones, such as, for example, troglitazone (also known as CS-045 (Sankyo) and CI-991 (Park-Davis)), pioglitazone (also known as AD-4833 and U-72107E), rosiglitazone (also known as BRL49653), englitazone (also known as CP-68,722), and ciglitazone.

In another aspect, the present invention provides new compounds, pharmaceutical compositions and methods relating to the new compounds, or their pharmaceutically acceptable salts, for inhibiting a telomerase enzyme, comprising contacting the telomerase enzyme with a compound, or its pharmaceutically acceptable salt, having the formula (I):

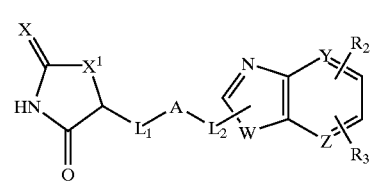

wherein X is O or S; $X_1$ is O, N or S; $L_1$ is a direct bond, —$CHR_1$—, or =$CR_1$—, wherein $R_1$ is H or alkyl, such as lower alkyl; A is a direct bond, alkyl, aryl, aralkyl or heteroaryl; $L_2$ is a direct bond or a linking group having from 1 to 3 atoms independently selected from unsubstituted or substituted carbon, N, O or S W is selected from the group consisting of O, $NR_5$, and S, wherein $R_5$ is selected from the group consisting of H, alkyl, aryl, and aralkyl; Y and Z are independently 10.1 selected to be C or N; and $R_2$, $R_3$ and $R_4$ are independently selected from the group consisting of hydrogen, hydroxyl, halogen, alkyl, aryl, alkoxyl, cyano, nitro, and heteroaryl.

In the compounds of formula (I) above, $L_1$ and $L_2$ may be direct single bonds, or may be linking groups. Representative linking groups useful in the compounds of the invention include, for example, —O—, —S—, —NH—, —$CH_2$—, —$OCH_2$—, —OC(O)—, —$CO_2$—, —NHC(O)—, —C(O)NH—, —OC(O)$CH_2$—, —OC(O)NH—, —$SO_2$—NH—, and —NHC(O)NH—. In certain embodiments, $L_1$ is —$CHR_1$— or =$CR_1$—, as represented by the formula (II) below:

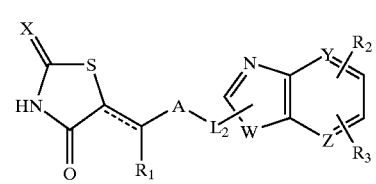

wherein --- is a single or double bond and $R_1$ is hydrogen, alkyl, or lower alkyl.

As noted above, A may be phenyl to form, for example, an aryl moiety. Alternatively, A may be heteroaryl, such as, for example, pyridine, quinoline, isoquinoline, thiophene, furan, naphthalene, indene, indole, imidazole, benzimidazole, pyrazole, and the like, wherein the heteroaryl may be substituted or unsubstituted. In one embodiment, A is phenyl. In another embodiment, at least one of $R_2$ or $R_3$ is other than hydrogen. In another embodiment, at least one of $R_2$ and $R_3$ is halo, and preferably both $R_2$ and $R_3$ are halo to form a dihalo-substituted phenyl moiety. In another embodiment, at least one of $R_2$, $R_3$, or $R_5$ is a thiazolidinone substituent having the formula (III):

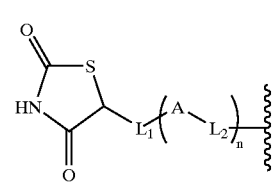

wherein $L_1$, $L_2$, and A are as defined above, and n is 0 or 1. Compounds having the thiazolidinone derivative have the structure shown in formula (IV) below:

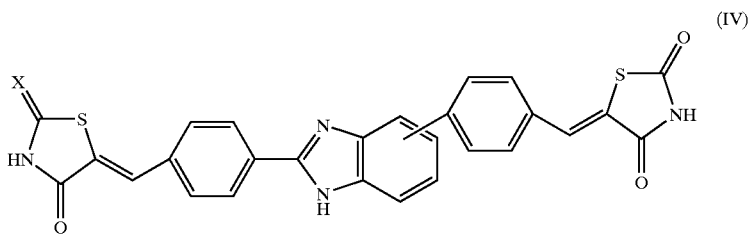

(IV)

In certain embodiments, the new compounds of the present invention have the general structure (V) shown below:

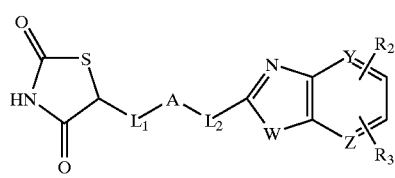

(V)

and their pharmaceutically acceptable salts, wherein $L_1$ is a direct bond, —$CHR_1$—, or =$CR_1$—, wherein $R_1$ is H or alkyl; A is aryl or heteroaryl; $L_2$ is a direct single bond or a linking group having from 1 to 3 atoms independently selected from unsubstituted or substituted carbon, N, O or S; W is selected from the group consisting of O $NR_5$, and S, wherein $R_5$ is selected from the group consisting of H, alkyl, aryl, and aralkyl; Y and Z are independently selected to be C or N;

and $R_2$ and $R_3$ and $R_4$ are independently selected from the group consisting of hydrogen, hydroxyl, halogen, alkyl, aryl, alkoxyl, cyano, nitro, and heteroaryl. In certain embodiements, W is $NR_5$, where $R_5$ can be H, lower alkyl such as methyl, ethyl, propyl, butyl, allyl, ethoxycarbonyl methyl, 2-(dimethylamino)ethyl, and the like, aralkyl such as benzyl, 3,4-dichlorobenzyl, 4-formylbenzyl, 4-methoxycarbonyl benzyl, 2-naphtylmethyl, and 5-chlorothiophen-2-ylmethyl, aryl, or heteroaryl. Some representative compounds of formula (V) wherein $L_1$ is =CH— and A is phenyl are shown below in Scheme I.

SCHEME 1

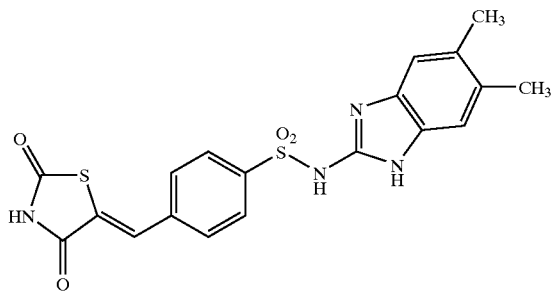

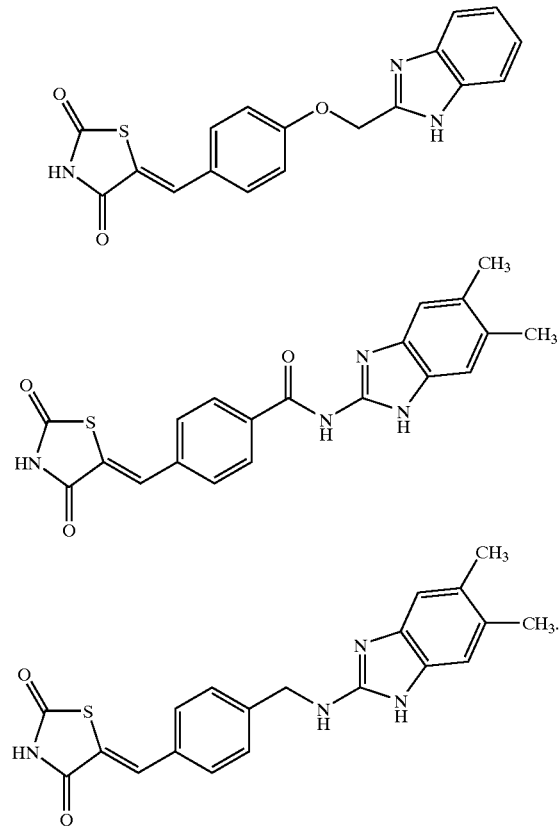

In another embodiment, the new compounds of the present invention have the general structure (VI) shown below:

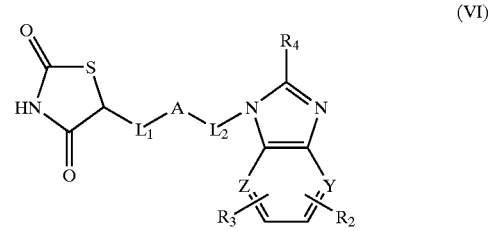

(VI)

and its pharmaceutically acceptable salts, wherein $L_1$ is a direct bond, —$CHR_1$—, or =$CR_1$—, wherein $R_1$ is H or alkyl; A is aryl or heteroaryl; $L_2$ is a direct single bond or a linking group having from 1 to 3 atoms independently selected from unsubstituted or substituted carbon, N, O or S; W is selected from the group consisting of O, $NR_5$, and S, wherein $R_5$ is selected from the group consisting of H, alkyl, aryl, and aralkyl; Y and Z are independently selected to be C or N; and $R_2$, $R_3$ and $R_4$ are independently selected from the group consisting of hydrogen, hydroxyl, halogen, alkyl, aryl, alkoxyl, cyano, nitro, and heteroaryl. In certain embodiments, anyone of $R_2$, $R_3$ or $R_4$ can be a thiazolidinone substituent represented by formula (III).

In another embodiment, the new compounds of the invention have the general structure (VII) shown below:

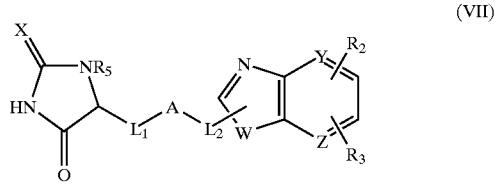

(VII)

and its pharmaceutically acceptable salts, wherein X, $L_1$, A, $L_2$, W, Y, Z, $R_2$, $R_3$ and $R_5$ are as described above.

Compounds of formula above, wherein $L_1$ is $=CR_1-$, can be obtained by reacting a thiazolidine derivative with an aromatic carbonyl compound. The reaction can be carried out optionally in the presence of a base catalyst and optionally in a solvent. The base catalyst, usually present in about 0.1 to about 2 equivalent, may be piperidine, piperidinium acetate, diethylamine, pyridine, sodium acetate, potassium carbonate, sodium carbonate, and the like. The solvent may be an alcohol, such as methanol, ethanol, propanol, or the like, an ether, such as diethyl ether, tetrahydrofuran, dioxane, or the like, or a hydrocarbon, such as benzene, toluene, xylene, or the like, or polar such as N,N-dimethylformamide, N,N-dimethylacetamide, acetic acid, or the like and mixtures thereof. The reaction is carried out at a temperature of about room temperature to about 200° C., preferably about 50–100° C., and completes in about one hour to about 50 hours. Compounds where $L_1$ is $-CHR_1-$ can be synthesized by reducing the double bond of the compound made above. Typically, reduction is carried out with magnesium in methanol or hydrogenation is carried out using a noble metal catalyst, such as palladium, platinum, rhodium, or the like, as is well known in the art.

III. Synthesis of Telomerase Inhibitors

The compounds of the present invention can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $3^{rd}$ Ed., Vols. A and B (Plenum 1992), and Green and Wuts, PROTECTIVE GROUPS IN ORGANIC SYNTHESIS $2^{nd}$ Ed. (Wiley 1991). Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N. H.), Apin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.).

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification, identification and quantification are well known in the chemical arts.

Compounds of the invention can be synthesized using General Procedures 1, 2, and 3 described in detail in the Examples below. Detailed protocols from which the individual compounds described above can be synthesized are also provided in the Examples. The compounds where L is SO or $SO_2$ can be synthesised by oxidizing the corresponsing S compound in an inert solvent. The inert solvent may be dichloromethane, methanol, tetrahydrofuran, ether, hexane, toluene, cyclohexane, or the like, and mixtures thereof. The oxidizing agent may be m-chloroperbenzoic acid, hydrogen peroxide, or the like. The reaction is carried out at a temperature in the range of about −78 ° C. to the boiling point of the solvent, preferably from about 0° C. to about 30° C. for about 0.5 to about 12 hours.

IV. Anti-Tumor Activity of the Telomerase Inhibitors of the Invention

The compounds of the present invention demonstrate inhibitory activity against telomerase activity in vivo, as has been and can be demonstrated as described below. The in vitro activities of the compounds of the invention can also be demonstrated using the methods described herein. As used herein, the term "ex vivo" refers to tests performed using living cells in tissue culture.

One method used to identify compounds of the invention that inhibit telomerase activity involves placing cells, tissues, or preferably a cellular extract or other preparation containing telomerase in contact with several known concentrations of a test compound in a buffer compatible with telomerase activity. The level of telomerase activity for each concentration of test compound is measured and the $IC_{50}$ (the concentration of the test compound at which the observed activity for a sample preparation was observed to fall one-half of its original or a control value) for the compound is determined using standard techniques. Other methods for determining the inhibitory concentration of a compound of the invention against telomerase can be employed as will be apparent to those of skill in the art based on the disclosure herein.

With the above-described methods, $IC_{50}$ values for several of the compounds of the present invention were determined, and found to be below 100 $\mu$M.

With respect to the treatment of malignant diseases using the compounds described herein, compounds of the present invention are expected to induce crisis in telomerase-positive cell lines. Treatment of telomerase-positive cell lines, such as HEK-293 and HeLa cells, with a compound of the invention is also expected to induce a reduction of telomere length in the treated cells.

Compounds of the invention are also expected to induce telomere reduction during cell division in human tumor cell lines, such as the ovarian tumor cell lines OVCAR-5 and SK-OV-3. Importantly, however, in normal human cells used as a control, such as BJ cells of fibroblast origin, the observed reduction in telomere length is expected to be no different from cells treated with a control substance, e.g., dimethyl sulfoxide (DMSO). The compounds of the invention also are expected to demonstrate no significant cytotoxic effects at concentrations below about 5 µM in the normal cells.

In addition, the specificity of the compounds of the present invention for telomerase can be determined by comparing their activity ($IC_{50}$) with respect to telomerase to other enzymes having similar nucleic acid binding or modifying activity similar to telomerase in vitro. Such enzymes include DNA Polymerase I, HeLa RNA Polymerase II, T3 RNA Polymerase, MMLV Reverse Transcriptase, Topoisomerase I, Topoisomerase II, Terminal Transferase and Single-Stranded DNA Binding Protein (SSB). Compounds having lower $IC_{50}$ values for telomerase as compared to the $IC_{50}$ values toward the other enzymes being screened are said to possess specificity for telomerase.

In vivo testing can also be performed using a mouse xenograft model, for example, in which OVCAR-5 tumor cells are grafted onto nude mice, in which mice treated with a compound of the invention are expected to have tumor masses that, on average, may increase for a period following the initial dosing, but will begin to shrink in mass with continuing treatment. In contrast, mice treated with a control (e.g., DMSO) are expected to have tumor masses that continue to increase.

From the foregoing those skilled in the art will appreciate that the present invention also provides methods for selecting treatment regimens involving administration of a compound of the invention. For such purposes, it may be helpful to perform a terminal restriction fragment (TRF) analysis in which DNA from tumor cells is analyzed by digestion with restriction enzymes specific for sequences other than the telomeric $(T_2 AG_3)_N$ sequence. Following digestion of the DNA, gel electrophoresis is performed to separate the restriction fragments according to size. The separated fragments are then probed with nucleic acid probes specific for telomeric sequences to determine the lengths of the terminal fragments containing the telomere DNA of the cells in the sample. By measuring the length of telomeric DNA, one can estimate how long a telomerase inhibitor should be administered and whether other methods of therapy (e.g., surgery, chemotherapy and/or radiation) should also be employed. In addition, during treatment, one can test cells to determine whether a decrease in telomere length over progressive cell divisions is occurring to demonstrate treatment efficacy.

V. Telomerase Inhibiting Compositions and Methods for Treating Diseases

The present invention also provides pharmaceutical compositions for inhibiting cell proliferation of telomerase positive cells, and treating cancer and other conditions in which inhibition of telomerase is an effective therapy. These compositions include a therapeutically effective amount of a telomerase inhibiting compound of the invention in a pharmaceutically acceptable carrier or salt.

In one embodiment, the present invention provides methods, compounds and compositions for inhibiting a telomerase enzyme, inhibiting proliferation of telomerase postive cells, and for treating cancer in a mammal. The compositions of the invention include a therapeutically effective amount of a compound of the invention (or a pharmaceutically acceptable salt thereof) in a pharmaceutically acceptable carrier. The compounds and compositions of the present invention may also be used for the treatment of other telomerase mediated conditions or diseases, such as, for example, other hyperproliferative or autoimmune disorders such as psoriasis, rheumatoid arthritis, immune system disorders requiring immune system suppression, immune system reactions to poison ivy or poison oak, and the like.

In addition, it will be appreciated that therapeutic benefits for treatment of cancer can be realized by combining a telomerase inhibitor of the invention with other anti-cancer agents, including other inhibitors of telomerase such as described in U.S. Pat. Nos. 5,656,638, 5,760,062, 5,767,278, 5,770,613 and 5,863,936. The choice of such combinations will depend on various factors including, but not limited to, the type of disease, the age and general health of the patient, the aggressiveness of disease progression, the TRF length and telomerase activity of the diseased cells to be treated and the ability of the patient to tolerate the agents that comprise the combination. For example, in cases where tumor progression has reached an advanced state, it may be advisable to combine a telomerase inhibiting compound of the invention with other agents and therapeutic regimens that are effective at reducing tumor size (e.g. radiation, surgery, chemotherapy and/or hormonal treatments). In addition, in some cases it may be advisable to combine a telomerase inhibiting agent of the invention with one or more agents that treat the side effects of a disease, e.g., an analgesic, or agents effective to stimulate the patient's own immune response (e.g., colony stimulating factor).

In one such method, a pharmaceutical formulation comprises a telomerase inhibitor of the invention with an anti-angiogenesis agent, such as fumagillin, fumagillin derivatives, or AGM-1470. The latter compound is available from Takeda Chemical Industries, Ltd., while the former compounds are described in Ingber, et al., Dec. 6, 1990, "Synthetic analogues of fumagillin that inhibit angiogenesis and suppress tumor growth", Nature 348:555–557. Other combinations may include, but are not limited to, a telomerase inhibitor of the invention in addition to one or more antineoplastic agents or adjuncts (e.g., folinic acid or mesna).

Antineoplastic agents suitable for combination with the compounds of the present invention include, but are not limited to, alkylating agents including alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophosphoramide and trimethylolmelamine; nitrogen mustards such as chlorambucil, chlomaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine and ranimustine. Additional agents include dacarbazine, mannomustine, mitobronitol, mitolactol and pipobroman. Still other classes of relevant agents include antibiotics, hormonal antineoplastics and antimetabolites. Yet other combinations will be apparent to those of skill in the art.

Additional agents suitable for combination with the compounds of the present invention include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, -sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, α-amanitine ;3 and other fungal amatoxins, cordycepin (3'-deoxyadenosine), dichlororibofuranosyl benzimidazole, rifampicine, streptovaricin and streptolydigin also can be combined with the compounds of the invention to provide pharmaceutical compositions.

In another embodiment, the present invention includes compounds and compositions in which a telomerase inhibitor is either combined with or covalently bound to a cytotoxic agent bound to a targeting agent, such as a monoclonal antibody (e.g., a murine or humanized monoclonal antibody). It will be appreciated that the latter combination may allow the introduction of cytotoxic agents into cancer cells with greater specificity. Thus, the active form of the cytotoxic agent (i.e., the free form) will be present only in cells targeted by the antibody. Of course, the telomerase inhibitors of the invention may also be combined with monoclonal antibodies that have therapeutic activity against cancer.

In addition to the application of the telomerase inhibitors of the present invention to the treatment of mammalian diseases characterized by telomerase activity, telomerase inhibitors such as those disclosed herein, can be applied to agricultural phytopathogenic organisms that are characterized by telomerase activity. These organisms include nematodes such as *Ceanorhabditis elegans*, in which telomerase activity has been found, and in fungi which are expected to have telomerase activity based on the determination that the DNA of the fungus *Ustilago maydis* exhibits telomeres having the tandem TTAGGG repeats that are maintained by telomerase. Also, protozoans have TTAGGG telomeres and cause human disease. The telomerase-inhibiting compounds of the invention can be administered to plants and soil infected with phytopathogenic organisms having telomerase activity alone, or in combination with other telomerase-inhibiting agents and/or other agents used to control plant diseases. The determination of the compositions used to control such phytopathogenic organisms and the appropriate modes of delivering such compositions will be known to those having skill in the agricultural arts.

The determination that nematodes, protozoans and possibly fungi have telomerase activity also indicates that the telomerase inhibitors provided by the present invention can be used to treat nematode infections in humans and animals of veterinary interest such as dogs and cats. Nematode infection in humans and animals often is in the form of hookworm or roundworm infection and leads to a host of deadly secondary illnesses such as meningitis, myocarditis, and various neurological diseases. Thus, it will be appreciated that administration of the telomerase-inhibiting compounds such as those of the invention, alone, or in combination with other telomerase-inhibiting agents and/or other therapeutic agents, can be used to control nematode, protozoan and fungal infections in humans and animals.

In general, a suitable effective dose of a compound of the invention will be in the range of 0.001 to 1000 milligram (mg) per kilogram (kg) of body weight of the recipient per day, preferably in the range of 0.001 to 100 mg per kg of body weight per day, more preferably between about 0.1 and 100 mg per kg of body weight per day and still more preferably in the range of between 0.1 to 10 mg per kg of body weight per day. The desired dosage is preferably presented in one, two, three, four, or more subdoses administered at appropriate intervals throughout the day, or by the action of a continuous pump. These subdoses can be administered as unit dosage form, for example, containing 5 to 10,000 mg, preferably 10 to 1000 mg of active ingredient per unit dosage from. Preferably, the dosage is presented once per day at a dosing at least equal to TID, or is administered using a continuous pump delivery system.

The composition used in these therapies can be in a variety of forms. These include, for example, solid, semi-solid, and liquid dosage forms, such as tablets, pills, powders, liquid solutions or suspensions, liposomes, and injectable and infusible solutions. The preferred form depends on the intended mode of administration and therapeutic application. The compositions also preferably include conventional pharmaceutically acceptable carriers and adjuvants, as is well known to those of skill in the art. See, e.g., REMINGTON'S PHARMACEUTICAL SCIENCES, Mack Publishing Co.: Easton, Pa., 17th Ed. (1985). Preferably, administration will be by oral or parenteral (including subcutaneous, intramuscular, intravenous, and intradermal) routes. More preferably, the route of administration will be oral. The therapeutic methods and agents of this invention can of course be used concomitantly or in combination with other methods and agents for treating a particular disease or disease condition.

While it is possible to administer the active ingredient of this invention alone, it is preferable to present a therapeutic agent as part of a pharmaceutical formulation or composition. The formulations of the present invention comprise at least one telomerase activity-inhibiting compound of this invention in a therapeutically or pharmaceutically effective dose together with one or more pharmaceutically or therapeutically acceptable carriers and optionally other therapeutic ingredients. Various considerations for preparing such formulations are described, e.g., in Gilman et al. (eds.) GOODMAN AND GILMAN'S: THE PHARMACOLOGICAL BASES OF THERAPEUTICS, 8th Ed., Pergamon Press (1990); and REMINGTON'S supra. Methods for administration are discussed therein, e.g., for oral, intravenous, intraperitoneal, intramuscular, and other forms of administration. Typically, methods for administering pharmaceutical compositions will be either topical, parenteral, or oral administration methods for prophylactic and/or therapeutic treatment. Oral administration is preferred. The pharmaceutical compositions can be administered in a variety of unit dosage forms depending upon the method of administration. As noted above, unit dosage forms suitable for oral administration include powders, tablets, pills, and capsules.

One can use topical administration to deliver a compound of the invention by percutaneous passage of the drug into the systemic circulation of the patient. The skin sites include anatomic regions for transdermally administering the drug, such as the forearm, abdomen, chest, back, buttock, and mastoidal area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin.

A variety of transdermal drug delivery devices can be employed with the compounds of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating. See, e.g., U.S. Pat. Nos. 4,310,509; 4,560,555; and 4,542,012.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir. See, e.g., U.S. Pat. Nos. 4,597,961; 4,485,097; 4,608,249; 4,505,891; 3,843,480; 3,948,254; 3,948,262; 3,053,255; and 3,993,073.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material. See, e.g., U.S. Pat. Nos. 4,542,013; 4,460,562; 4,466,953; 4,482,534; and 4,533,540.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like. Topical administration of compounds of the invention may also be preferred for treating diseases such as skin cancer and fungal infections of the skin (pathogenic fungi typically express telomerase activity).

The topical pharmaceutical compositions according to this invention may also include one or more preservatives or bacteriostatic agents, e.g., methyl hydroxybenzoate, propyl hydroxybenzoate, chlorocreosol, benzalkonium chlorides, and the like. The topical pharmaceutical compositions also can contain other active ingredients such as antimicrobial agents, particularly antibiotics, anesthetics, analgesics, and antipruritic agents.

The compounds of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption. Note that certain such routes may be used even where the patient is unable to ingest a treatment composition orally. Note also that where delivery of a telomerase inhibitor of the invention would be enhanced, one can select a composition for delivery to a mucosal membrane, e.g., in cases of colon cancer one can use a suppository to deliver the telomerase inhibitor.

For delivery to the buccal or sublingual membranes, typically an oral formulation, such as a lozenge, tablet, or capsule, will be used. The method of manufacture of these formulations is known in the art, including, but not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa.

Parenteral administration is generally characterized by injection, either subcutaneously, intramuscularly, or intravenously. Thus, this invention provides compositions for intravenous administration that comprise a solution of a compound of the invention dissolved or suspended in an acceptable carrier. Injectables can be prepared in conventional forms, either as liquid solutions or suspensions, solid forms suitable for solution or suspension in liquid prior to injection, or as emulsions. Suitable excipients are, for example, water, buffered water, saline, dextrose, glycerol, ethanol, or the like. These compositions will be sterilized by conventional, well known sterilization techniques, such as sterile filtration. The resulting solutions can be packaged for use as is or lyophilized, the lyophilized preparation being combined with a sterile solution prior to administration. In addition, if desired, the pharmaceutical compositions to be administered may also contain minor amounts of non-toxic auxiliary substances, such as wetting or emulsifying agents, pH buffering agents and the like, such as for example, sodium acetate, sorbitan monolaurate, triethanolamine oleate, etc. Such formulations will be useful in treating ovarian cancers.

Another method of parenteral administration employs the implantation of a slow-release or sustained-release system, such that a constant level of dosage is maintained. See, e.g., U.S. Pat. No. 3,710,795.

Liquid pharmaceutically administrable compositions can, for example, be prepared by dissolving, dispersing, etc., an active compound as defined above and optional pharmaceutical adjuvants in an excipient, such as, for example, water, saline, aqueous dextrose, glycerol, ethanol, olive oil, and other lipophilic solvents, and the like, to form a solution or suspension. If desired, the pharmaceutical composition to be administered may also contain minor amounts of nontoxic auxiliary substances, such as wetting or emulsifying agents, pH buffering agents, and the like, for example, sodium acetate, sorbitan monolaurate, triethanolamine sodium acetate, triethanolamine oleate, etc. Actual methods of preparing such dosage forms are known and will be apparent to those skilled in this art; for example, see REMINGTON'S PHARMACEUTICAL SCIENCES, supra. The composition or formulation to be administered will contain an effective amount of an active compound of the invention.

For solid compositions, conventional nontoxic solid carriers can be used and include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

The compositions containing the compounds of the invention can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

In addition to internal (in vivo) administration, the compounds and compositions of the invention may be applied ex vivo to achieve therapeutic effects, as for example, in the case of a patient suffering from leukemia. In such an application, cells to be treated, e.g., blood or bone marrow cells, are removed from a patient and treated with a pharmaceutically effective amount of a compound of the invention. The cells are returned to the patient following treatment. Such a procedure can allow for exposure of cells to concentrations of therapeutic agent for longer periods or at higher concentrations than otherwise available.

Once improvement of the patient's conditions has occurred, as, for example, by the occurrence of remission in the case of a cancer patient, a maintenance dose is administered if necessary. Subsequently, the dosage or the frequency of administration, or both, can be reduced, as a function of the systems, to a level at which the improved condition is retained. When the symptoms have been alleviated to the desired level, treatment can cease. Patients can, however, require additional treatment upon any recurrence of the disease symptoms.

In prophylactic applications (e.g. chemoprevention), compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

As will be apparent to those of skill in the art upon reading of this disclosure, the present invention provides valuable reagents relating to human and mammalian telomerase. The above description of necessity provides a limited and merely illustrative sampling of specific compounds, and should not be construed as limiting the scope of the invention. Other features and advantages of the invention will be apparent from the following examples and claims.

EXAMPLES

The following examples describe specific aspects of the invention to illustrate the invention and also provide a description of methods that can be used to identify and test compounds that inhibit the activity of telomerase to aid those of skill in the art in understanding and practicing the invention. The examples should not be construed as limiting the invention in any manner.

General Procedure 1: Condensation of 2,4-Thiazolidinedione and Aldehyde

A mixture of appropriately substituted aldehyde (1 eq.), 2,4-thiazolidinedione (1.5 eq.) and piperidine (1.5 eq.) in ethanol was heated to reflux for 2–24 h. The resulting mixture was acidified with hydrochloric acid (1 mol/L). The precipitated products were filtered off and washed with water and/or ether to afford pure product. Alternatively, the acidified mixture was extracted with ethyl acetate or chloroform, organic phase washed with water and brine, dried over anhydrous sodium sulfate and concentrated under reduced pressure to yield crude product, which was purified either by column chromatography or recrystallization from appropriate solvent system.

General Procedure 2: Condensation of Aldehyde and Diamine to Afford Benzimidazole A mixture of aldehyde, diamine and 1,4-benzoquinone (1:1:1 molar ratio) in 1,4-dioxane was heated to 100° C. for 2–24 h. The mixture was cooled to room temperature, and the precipitated products were filtered off and washed with water and/or ether to afford pure product. Alternatively, the solvent was removed under reduced pressure and the resulting solid was recrystallized or triturated with appropriate solvent, such as ethyl acetate, ether, or 1,4-dioxane to afford pure product.

General Procedure 3: Alkylation of N1-position of 2-(4-Formylphenyl)benzimidzole To a solution of 2-(4-formylphenyl)benzimidazole (1 eq.) in dimethylformamide were added sodium hydride (1.5 eq.) and alkyl halides (2 eq.) at 0° C. under nitrogen atmosphere, and the mixture was stirred at 20–100° C. for 2–24 h. Water was added, and the precipitated products were collected by filtration and washed with water and or ether. Alternatively, the mixture was extracted with ethyl acetate, organic phase washed with water and brine, dried over anhydrous sodium sulfate and concentrated under reduced pressure to afford crude product, which was purified either by column chromatography or recrystallization from appropriate solvent system.

Example 1

Preparation of 5,6-Dichloro-2-[4-[(2,4-dioxothiazolidin-5-ylidene)methyl]phenyl]benzimidazole

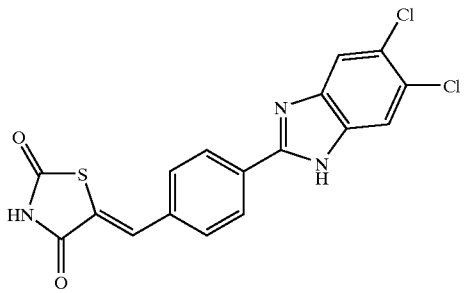

To a mixture of terephthalaldehyde mono-(diethyl acetal) (3.96 mL, 20.0 mmol) and 2,4-thiazolidinedione (2.81 g, 24.0 mmol) in ethanol (40 mL) was added piperidine (2.0 mL, 20.0 mmol). The reaction mixture was heated to reflux for 4 h. After cooling on an ice-bath, hydrochloric acid (0.2 mol/L, 100 mL) was added and the precipitated products were collected by filtration. The cake was washed with water and dried. To a solution of this product (5.50 g) in tetrahydrofuran (180 mL) was added hydrochloric acid (1 mol/L, 18 mL) and the mixture was stirred at room temperature for 2 h. Water was added, and the precipitated products were collected by filtration to give 5-(4-formylbenzylidene)-2,4-thiazolidinedione (3.91 g, 94%).

$^1$H NMR (400 MHz, DMSO-$d_6$) δ (ppm) 7.72 (d, J=8.1 Hz, 2H), 7.77 (s, 1H), 7.94 (d, J=7.7 Hz, 2H), 9.96 (s, 1H).

General Procedure 2 was then followed to obtain 5,6-dichloro-2-[4-[(2,4-dioxothiazolidin-5-ylidene)methyl]phenyl]benzimidazole.

$^1$H NMR (400 MHz, DMSO-$d_6$) δ (ppm) 7.72 (d, J=8.6 Hz, 2H), 7.74 (br s, 1H), 7.79 (s, 1H), 7.91 (br s, 1H), 8.23 (d, J=8.2 Hz, 2H), 12.7 (br s, 1H), 13.4 (br s, 1H); ESI–MS m/z 390, 388 (M–H)$^-$ $C_{17}H_9{}^{35}Cl_2N_3O_2S$=389.

Example 2

Preparation of 2-[4-[(2,4-Dioxothiazolidin-5-ylidene)methyl]phenyl]benzimidazole

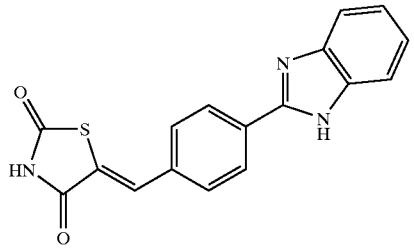

2-[4-[(2,4-Dioxothiazolidin-5-ylidene)methyl]phenyl]benzimidazole was prepared from 5-(4-formylbenzylidene)-2,4-thiazolidinedione and 1,2-phenylenediamine by following General Procedure 2.

ESI–MS m/z 320 (M–H)$^-$ $C_{17}H_{11}N_3O_2S$=321.

Example 3

Preparation of 5,6-Dimethyl-2-[4-[(2,4-dioxothiazolidin-5-ylidene)methyl]phenyl]benzimidazole

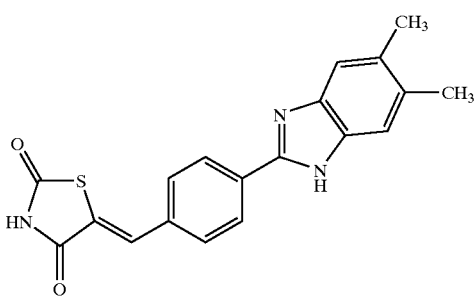

5,6-Dimethyl-2-[4-[(2,4-dioxothiazolidin-5-ylidene)methyl]phenyl]benzimidazole was prepared from 5-(4-formylbenzylidene)-2,4-thiazolidinedione and 4,5-dimethyl-1,2-phenylenediamine by following General Procedure 2.

ESI–MS m/z 348 (M–H)$^-$ $C_{19}H_{15}N_3O_2S$=349.

Example 4

Preparation of 2-[4-[(2,4-Dioxothiazolidin-5-ylidene)methyl]phenyl]-5-nitrobenzimidazole

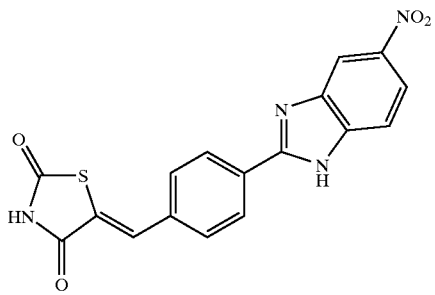

2-[4-[(2,4-Dioxothiazolidin-5-ylidene)methyl]phenyl]-5-nitrobenzimidazole was prepared from 5-(4-formylbenzylidene)-2,4-thiazolidinedione and 4-nitro-1,2-phenylenediamine by following General Procedure 2.

ESI–MS m/z 365 (M–H)$^-$ $C_{17}H_{10}N_4O_4S$=366.

Example 5

Preparation of 6-Chloro-2-[4-[(2,4-dioxothiazolidin-5-ylidene)methyl]phenyl]-4-(trifluoromethyl)benzimidazole

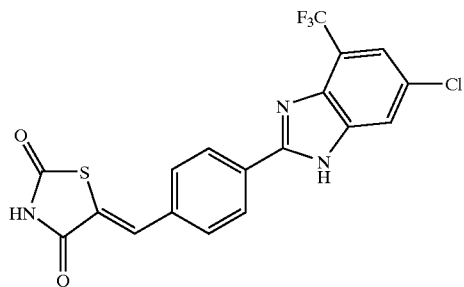

6-Chloro-2-[4-[(2,4-dioxothiazolidin-5-ylidene)methyl]phenyl]-4-(trifluoromethyl)benzimidazole was prepared from 5-(4-formylbenzylidene)-2,4-thiazolidinedione and 5-chloro-3-trifluoromethyl-1,2-phenylenediamine by following General Procedure 2.

ESI–MS m/z 423 (M–H)$^-$ $C_{18}H_9{}^{35}ClF_3N_3O_2S$=424.

Example 6

Preparation of 5-Benzoyl-2-[4-[(2,4-dioxothiazolidin-5-ylidene)methyl]phenyl]benzimidazole

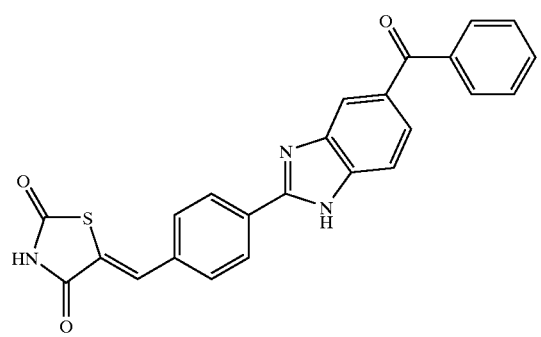

5-Benzoyl-2-[4-[(2,4-dioxothiazolidin-5-ylydene)methyl]phenyl]benzimidazole was prepared from 5-(4-formylbenzylidene)-2,4-thiazolidinedione and 3,4-diaminobenzophenone by following General Procedure 2.

ESI–MS m/z 424 (M–H)$^-$ $C_{24}H_{15}N_3O_3S$=425.

Example 7

Preparation of 2-[4-[(2,4-Dioxothiazolidin-5-ylidene)methyl]phenyl]-5-(trifluoromethyl)benzimidazole

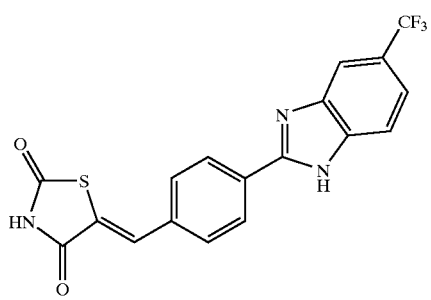

2-[4-[(2,4-Dioxothiazolidin-5-ylidene)methyl]phenyl]-5-trifluoromethylbenzimidazole was prepared from 5-(4-formylbenzylidene)-2,4-thiazolidinedione and 4-trifluoromethyl-1,2-phenylenediamine by following General Procedure 2.

ESI–MS m/z 388 (M–H)$^-$ $C_{18}H_{10}F_3N_3O_2S$=389.

Example 8

Preparation of 5-Cyano-2-[4-[(2,4-dioxothiazolidin-5-ylidene)methyl]phenyl]benzimidazole

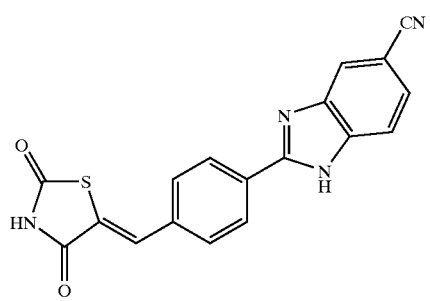

5-Cyano-2-[4-[(2,4-dioxothiazolidin-5-ylidene)methyl]phenyl]benzimidazole was prepared from 5-(4-formylbenzylidene)-2,4-thiazolidinedione and 3,4-diaminobenzonitrile by following General Procedure 2.

ESI–MS m/z 345 (M–H)$^-$ $C_{18}H_{10}N_4O_2S$=346.

Example 9

Preparation of 4,5-Dichloro-2-[4-[(2,4-dioxothiazolidin-5-ylidene)methyl]phenyl]benzimidazole

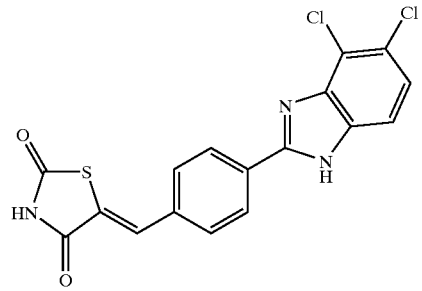

4,5-Dichloro-2-[4-[(2,4-dioxothiazolidin-5-ylidene)methyl]phenyl]benzimidazole was prepared from 5-(4-formylbenzylidene)-2,4-thiazolidinedione and 3,4-dichloro-1,2-phenylenediamine by following General Procedure 2.

ESI–MS m/z 390, 388 (M–H)$^-$ $C_{17}H_9Cl_2N_3O_2S$=389.

Example 10

Preparation of 4,6-Dichloro-2-[4-[(2,4-dioxothiazolidin-5-ylidene)methyl]phenyl]benzimidazole

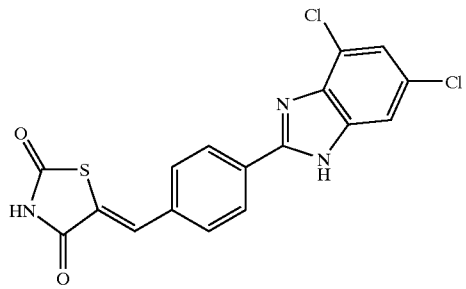

4,6-Dichloro-2-[4-[(2,4-dioxothiazolidin-5-ylidene)methyl]phenyl]benzimidazole was prepared from 5-(4-formylbenzylidene)-2,4-thiazolidinedione and 3,5-dichloro-1,2-phenylenediamine by following General Procedure 2.

ESI–MS m/z 390, 388 (M–H)$^-$ $C_{17}H_9Cl_2N_3O_2S$=389.

Example 11

Preparation of 5,6-Difluoro-2-[4-[(2,4-dioxothiazolidin-5-ylidene)methyl]phenyl]benzimidazole

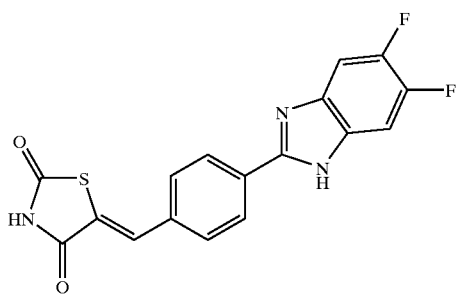

5,6-Difluoro-2-[4-[(2,4-dioxothiozolidin-5-ylidene)methyl]phenyl]benzimidazole was prepared from 5-(4-formylbenzylidene)-2,4-thiazolidinedione and 4,5-difluoro-1,2-phenylenediamine by following General Procedure 2.

ESI–MS m/z 356 (M–H)$^-$ $C_{17}H_9F_2N_3O_2S$=357.

Example 12

Preparation of 2-[4-[(2,4-Dioxothiazolidin-5-ylidene)methyl]phenyl]-4-hydroxybenzimidazole

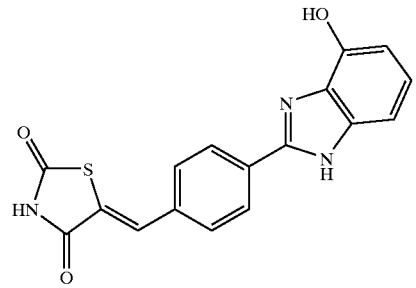

2-[4-[(2,4-Dioxothiazolidin-5-ylidene)methyl]phenyl]-4-hydroxybenzimidazole was prepared from 5-(4-formylbenzylidene)-2,4-thiazolidinedione and 2,3-diaminophenol by following General Procedure 2.

ESI–MS m/z 336 (M–H)$^-$ $C_{17}H_{11}N_3O_3S$=337.

Example 13

Preparation of 5,6-Dichloro-2-[4-(2,4-dioxothiazolidin-5-yl)phenyl]benzimidazole

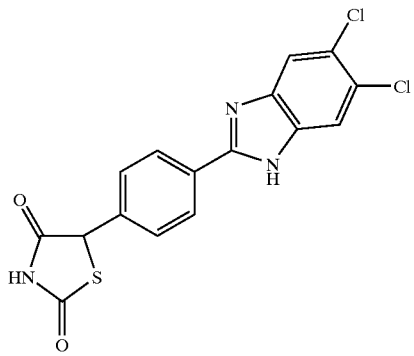

To a mixture of terephthalaldehyde mono-(diethyl acetal) (2.0 mL, 10 mmol), 4,5-dichloro-1,2-phenylenediamine (1.77 g, 10 mmol) and 1,4-benzoquinone (1.08 g, 10 mmol) in ethanol (50 mL) was heated to reflux for 6 h. The solvent was removed under reduced pressure. To the residue were added tetrahydrofuran (50 mL) and hydrochloric acid (1 mol/L, 10 mL), and the mixture was stirred at room temperature for 2 h. Water was added, and the mixture was extracted with ethyl acetate. The organic layer was washed with water and brine, and dried on anhydrous sodium sulfate. The solvent was removed under reduced pressure, and the residue was triturated with ether to afford 5,6-dichloro-2-(4-formylphenyl)benzimidazole (2.80 g, 97%).

$^1$H NMR (400 MHz, DMSO-$d_6$) δ (ppm) 7.87 (br s, 2H), 8.04 (d, J=8.6 Hz, 2H), 8.33 (d, J=8.2 Hz, 2H), 10.0 (s, 1H), 13.5 (br s, 1H); ESI–MS m/z 291, 289 (M–H)$^-$ $C_{14}H_8{}^{35}Cl_2N_2O$=290.

To a solution of 5,6-dichloro-2-(4-formylphenyl)benzimidazole (291 mg, 1.00 mmol) in tetrahydrofuran (40 mL) were added potassium cyanide (260 mg, 4.00 mmol), sodium hydrogen sulfite (500 mg), and water (10 mL). The mixture was stirred at room temperature for 12 h. Water was added, and the mixture was extracted with ethyl acetate. The organic layer was washed with brine and dried on anhydrous sodium sulfate. The solvent was removed under reduced pressure to afford 2-[4-[cyano(hydroxy)methyl]phenyl]-5,6-dichlorobenzimidazole (278 mg, 87%).

$^1$H NMR (400 MHz, DMSO-$d_6$) δ (ppm) 5.83 (d, J=6.2 Hz, 1H), 7.17 (d, J=6.2 Hz, 1H), 7.64 (d, J=8.2 Hz, 2H), 7.74 (br s, 1H), 7.91 (br s, 1H), 8.19 (d, J=8.6 Hz, 1H), 13.3 (br s, 1H).

ESI–MS m/z 318, 316 (M–H)$^-$ $C_{15}H_9{}^{35}Cl_2N_3O$=317.

To a suspension of 2-[4-[cyano(hydroxy)methyl]phenyl]-5,6-dichlorobenzimidazole (275 mg, 0.865 mmol) in tetrahydrofuran (20 mL) was added thionyl chloride (0.38 mL, 5.2 mmol), and the mixture was heated to reflux for 3 h. After cooling to room temperature, water was added and the mixture was extracted with ethyl acetate. The organic layer was washed with brine and dried on anhydrous sodium sulfate. The solvent was removed under reduced pressure. The residue was purified by column chromatography (14:1 chloroform/acetonitrile) to afford of 2-[4-[chloro(cyano)methyl]phenyl]-5,6-dichlorobenzimidazole (73 mg, 25%).

$^1$H NMR (400 MHz, DMSO-$d_6$) δ (ppm) 6.72 (s, 1H), 7.76 (d, J=8.2 Hz, 2H), 7.85 (br s, 2H), 8.25 (d, J=8.2 Hz, 2H); ESI–MS m/z 336, 334 (M–H)$^-$ $C_{15}H_8{}^{35}Cl_3N_3$=335.

To a solution of of 2-[4-[chloro(cyano)methyl]phenyl]-5,6-dichlorobenzimidazole (22 mg, 0.065 mmol) in ethanol (5 mL) was added thiourea (10 mg, 0.13 mmol), and the mixture heated to reflux for 1 h. Hydrochloric acid (2 mol/L, 4 mL) was added, and the mixture was heated to reflux for additional 11 h. After cooling to room temperature, pH was adjusted to 10, and the mixture was washed with ethyl acetate. The mixture was acidified, and extracted with ethyl acetate. The organic layer was washed with brine and dried on anhydrous sodium sulfate. The solvent was removed under reduced pressure to afford 5,6-dichloro-2-[4-(2,4-dioxothiazolidin-5-yl)phenyl]benzimidazole (7.0 mg, 28%).

$^1$H NMR (400 MHz, DMSO-$d_6$) δ (ppm) 5.85 (s, 1H), 7.59 (d, J=8.6 Hz, 2H), 7.73 (s, 1H), 7.91 (s, 1H), 8.14 (d, J=8.6 Hz, 2H), 12.4 (br s, 1H), 13.3 (br s, 1H); ESI–MS m/z 378, 376 (M–H)$^-$, $C_{16}H_9{}^{35}Cl_2N_3O_2S$=377.

Example 14

Preparation of 1-(3,4-Dichlorobenzyl)-2-[4-[(2,4-dioxothiazolidin-5ylidene)methyl]-phenyl]benzimidazole

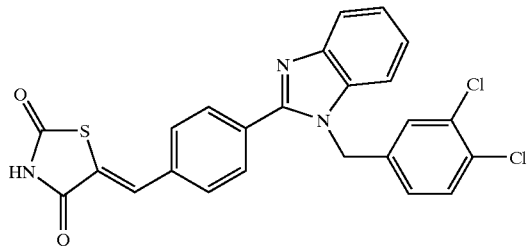

2-(4-Formylphenyl)benzimidazole was prepared from terephthalaldehyde mono-(diethyl acetal) and phenylenediamine in a similar manner as described in Example 13.

General Procedure 3 was then followed to obtain 1-(3,4-dichlorobenzyl)-2-(4-formylphenyl)benzimidazole from 2-(4-formylphenyl)benzimidazole and 3,4-dichlorobenzyl chloride.

General Procedure 1 was then followed to obtain 1-(3,4-dichlorobenzyl)-2-[4-[(2,4-dioxothiazolidin-5-ylidene)methyl]phenyl]benzimidazole.

ESI–MS m/z 480, 478 (M–H)$^-$, $C_{24}H_{15}{}^{35}Cl_2N_3O_2S$=479.

Example 15

Preparation of 1-(3,4-Dichlorobenzyl)-5,6-dimethyl-2-[4-[(2,4-dioxothiazolidin-5-ylidene)methyl]phenyl]benzimidazole

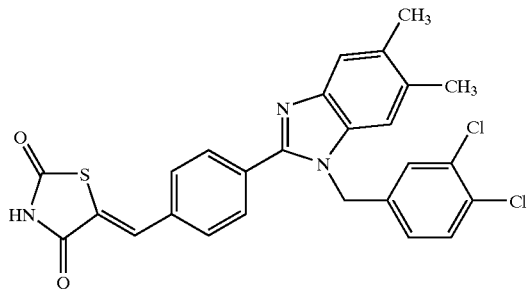

5,6-Dimethyl-2-(4-formylphenyl)benzimidazole was prepared from terephthalaldehyde mono-(diethyl acetal) and 5,6-dimethyl-1,2-phenylenediamine in a similar manner as described in Example 13.

General Procedure 3 was then followed to obtain 1-(3,4-dichlorobenzyl)-5,6-dimethyl-2-(4-formylphenyl)benzimidazole from 5,6-dimethyl-2-(4-formylphenyl)benzimidazole and 3,4-dichlorobenzyl chloride.

General Procedure 1 was then followed to obtain 1-(3,4-dichlorobenzyl)-5,6-dimethyl-2-[4-[(2,4-dioxothiazolidin-5-ylidene)methyl]phenyl]benzimidazole.

ESI–MS m/z 508, 506 (M–H)$^-$, $C_{26}H_{19}{}^{35}Cl_2N_3O_2S$=507.

Example 16

Preparation of 5,6-Dichloro-1-(3,4-dichlorobenzyl)-2-[4-[(2,4-dioxothiazolidin-5-ylidene)methyl]phenyl]benzimidazole

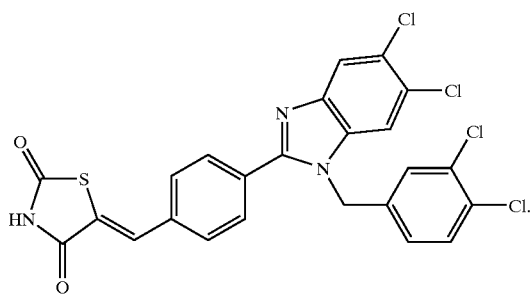

5,6-Dichloro-1-(3,4-dichlorobenzyl)-2-(4-formylphenyl)benzimidazole was prepared from 5,6-dichloro-2-(4-formylphenyl)benzimidazole obtained in Example 13 and 3,4-diclorobenzyl chloride by following General Procedure 3.

General Procedure 1 was then followed to obtain 5,6-dichloro-1-(3,4-dichlorobenzyl)-2-[4-[(2,4-dioxothiazolidin-5-ylidene)methyl]phenyl]benzimidazole.

ESI–MS m/z 548, 546 (M–H)$^-$, $C_{24}H_{13}{}^{35}Cl_4N_3O_2S$=547.

Example 17

Preparation of 5,6-Dichloro-2-[4-[(2,4-dioxothiazolidin-5-ylidene)methyl]phenyl]-1-methylbenzimidazole

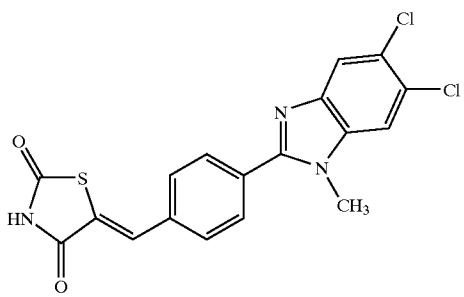

5,6-Dichloro2-(4-formylphenyl)-1-methylbenzimidazole was prepared from 5,6-dichloro-2-(4-formylphenyl)benzimidazole obtained in Example 13 and iodomethane by following General Procedure 3.

General Procedure 1 was then followed to obtain 5,6-dichloro-2-[4-[(2,4-dioxothiazolidin-5-ylidene)methyl]phenyl]-1-methylbenzimidazole.

ESI–MS m/z 404, 402 (M–H)$^-$, $C_{18}H_{11}{}^{35}Cl_2N_3O_2S$=403.

Example 18

Preparation of 1-Butyl-5,6-dichloro-2-[4-[(2,4-dioxothiazolidin-5-ylidene)methyl]phenyl]benzimidazole

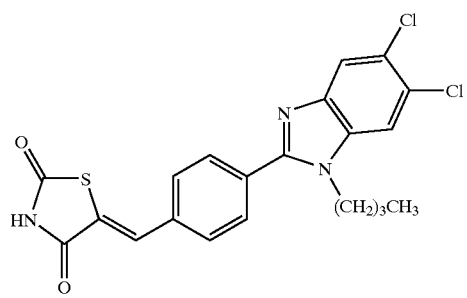

1-Butyl-5,6-dichloro2-(4-formylphenyl)benzimidazole was prepared from 5,6-dichloro-2-(4-formylphenyl)benzimidazole obtained in Example 13 and 1-iodobuthane by following General Procedure 3.

General Procedure 1 was then followed to obtain 1-butyl-5,6-dichloro-2-[4-[(2,4-dioxothiazolidin-5-ylidene)methyl]phenyl]benzimidazole.

ESI–MS m/z 446, 444 (M–H)$^-$, $C_{21}H_{17}{}^{35}Cl_2N_3O_2S$=445.

Example 19

Preparation of 1-Allyl-5,6-dichloro-2-[4-[(2,4-dioxothiazolidin-5-ylidene)methyl]-phenyl]benzimidazole

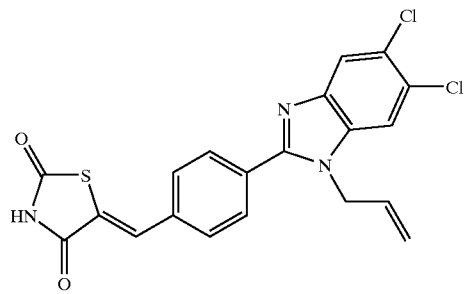

1-Allyl-5,6-dichloro2-(4-formylphenyl)benzimidazole was prepared from 5,6-dichloro-2-(4-formylphenyl)benzimidazole obtained in Example 13 and allylbromide by following General Procedure 3.

General Procedure 1 was then followed to obtain I-allyl-5,6-dichloro-2-[4-[(2,4-dioxothiazolidin-5-ylidene)methyl]phenyl]benzimidazole.

ESI–MS m/z 430, 428 (M–H)$^-$, $C_{20}H_{13}{}^{35}Cl_2N_3O_2S$=429.

Example 20

Preparation of Ethyl [5,6-Dichloro-2-[4-[(2,4-dioxothiazolidin-5-ylidene)methyl]phenyl]-benzimidazol-1-yl]acetate

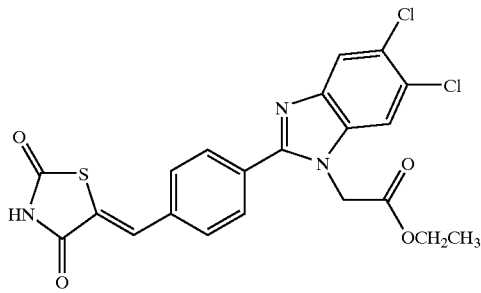

Ethyl [5,6-dichloro2-(4-formylphenyl)benzimidazol-1-yl]acetate was prepared from 5,6-dichloro-2-(4-formylphenyl)benzimidazole obtained in Example 13 and ethyl bromoacetate by following General Procedure 3.

General Procedure 1 was then followed to obtain ethyl [5,6-dichloro-2-[4-[(2,4-dioxothiazolidin-5-ylidene)methyl]phenyl]benzimidazol-1-yl]acetate.

ESI–MS m/z 476, 474 (M–H)$^-$, $C_{21}H_{15}{}^{35}Cl_2N_3O_4S=475$.

Example 21

Preparation of 5,6-Dichloro-1-(2-dimethyaminoethyl)-2-[4-[(2,4-dioxothiazolidin-5-ylidene)methyl]phenyl]benzimidazole

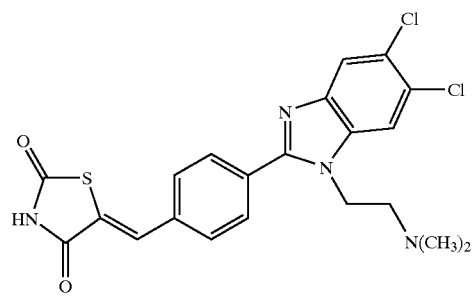

5,6-Dichloro-1-(2-dimethylaminoethyl)-2-(4-formylphenyl)benzimidazole was prepared from 5,6-dichloro-2-(4-formylphenyl)benzimidazole obtained in Example 13 and 2-(dimethylamino)ethyl chloride hydrochloride by following General Procedure 3.

General Procedure 1 was then followed to obtain 5,6-dichloro-1-(2-dimethyaminoethyl)-2-[4-[(2,4-dioxothiazolidin-5-ylidene)methyl]phenyl]benzimidazole.

ESI–MS m/z 461, 459 (M–H)$^-$, $C_{21}H_{18}{}^{35}Cl_2N_4O_2S=460$.

Example 22

Preparation of 1-Benzyl-5,6-dichloro-2-[4-[(2,4-dioxothiazolidin-5-ylidene)methyl]phenyl]benzimidazole

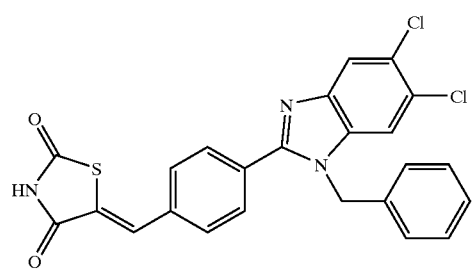

1-Benzyl-5,6-dichloro2-(4-formylphenyl)benzimidazole was prepared from 5,6-dichloro-2-(4-formylphenyl)benzimidazole obtained in Example(138326) and benzyl bromide by following General Procedure 3.

General Procedure 1 was then followed to obtain 1-benzyl-5,6-dichloro-2-[4-[(2,4-dioxothiazolidin-5-ylidene)methyl]phenyl]benzimidazole.

ESI–MS m/z 480, 478 (M–H)$^-$, $C_{24}H_{15}{}^{35}Cl_2N_3O_2S=479$.

Example 23

Preparation of Methyl 4-[5,6-Dichloro-2-[4-[(2,4-dioxothiazolidin-5-ylidene)methyl]phenyl]benzimidazol-1-ylmethyl]benzoate

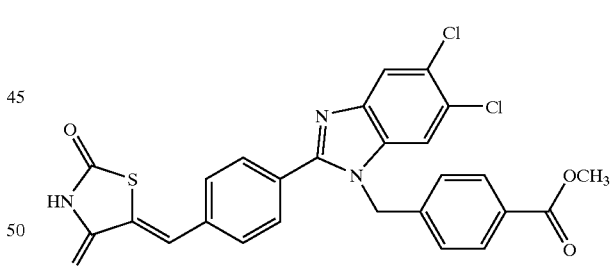

Methyl 4-[5,6-dichloro2-(4-formylphenyl)benzimidazol-1-ylmethyl]benzoate was prepared from 5,6-dichloro-2-(4-formylphenyl)benzimidazole obtained in Example 13 and methyl 4-bromomethylbenzoate by following General Procedure 3.

General Procedure 1 was then followed to obtain methyl 4-[5,6-dichloro-2-[4-[(2,4-dioxothiazolidin-5-ylidene)methyl]phenyl]benzimidazol-1-ylmethyl]benzoate.

ESI–MS m/z 538, 536 (M–H)$^-$, $C_{26}H_{17}{}^{35}Cl_2N_3O_4S=537$.

Example 24

Preparation of 5,6-Dichloro-2-[4-[(2,4-dioxothiazolidin-5-ylidene)methyl]phenyl]-1-(2-naphthylmethyl)benzimidazole

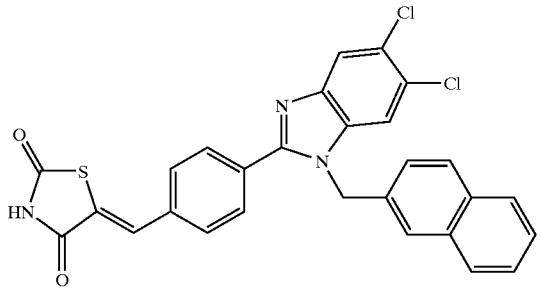

5,6-dichloro2-(4-formylphenyl)-1-(2-naphtylmethyl)benzimidazole was prepared from 5,6-dichloro-2-(4-formylphenyl)benzimidazole obtained in Example 13 and 2-chloromethylnaphthalene by following General Procedure 3.

General Procedure 1 was then followed to obtain 5,6-dichloro-2-[4-[(2,4-dioxothiazolidin-5-ylidene)methyl]phenyl]-1-(2-naphthylmethyl)benzimidazole.

ESI–MS m/z 530, 528 (M–H)$^-$, $C_{28}H_{17}{}^{35}Cl_2N_3O_2S$=529.

Example 25

Preparation of 1-(5-chlorothiophen-2-ylmethyl)-5,6-dichloro-2-[4-[(2,4-dioxothiazolidin-5-ylidene)methyl]phenyl]benzimidazole

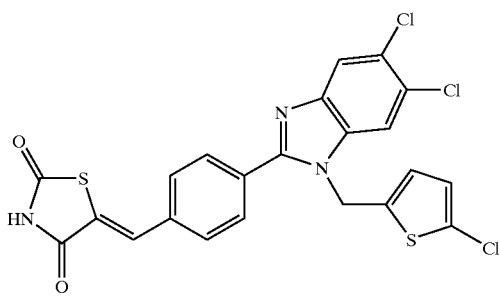

1-(5-Chlorothiophen-2-ylmethyl)-5,6-dichloro2-(4-formylphenyl)benzimidazole was prepared from 5,6-dichloro-2-(4-formylphenyl)benzimidazole obtained in Example 13 and 2-chloro-5-chloromethylthiophene by following General Procedure 3.

General Procedure 1 was then followed to obtain 1-(5-chlorothiophen-2-ylmethyl)-5,6-dichloro-2-[4-[(2,4-dioxothiazolidin-5-ylidene)methyl]phenyl]benzimidazole.

ESI–MS m/z 520, 518 (M–H)$^-$, $C_{22}H_{12}{}^{35}Cl_3N_3O_2S_2$=519.

Example 26

Preparation of 5,6-Dichloro-2-[4-[(2,4-dioxothiazolidin-5-ylidene)methyl]phenyl]-1-(quinolin-2-ylmethyl)benzimidazole

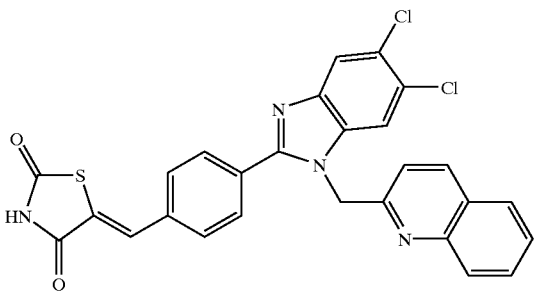

5,6-dichloro-2-(4-formylphenyl)-1-(quinolin-2-ylmethyl)benzimidazole was prepared from 5,6-dichloro-2-(4-formylphenyl)benzimidazole obtained in Example 13 and 2-chloromethylquinoline by following General Procedure 3.

General Procedure 1 was then followed to obtain 5,6-dichloro-2-[4-[(2,4-dioxothiazolidin-5-ylidene)methyl]phenyl]-1-(quinolin-2-ylmethyl)benzimidazole.

ESI–MS m/z 531, 529 (M–H)$^-$, $C_{27}H_{16}{}^{35}Cl_2N_4O_2S$=530.

Example 27

Preparation of 5,6-Dichloro-2-[4-[(2,4-dioxothiazolidin-5-ylidene)methyl]phenyl]-1-(thiazol-4-ylmethyl)benzimidazole

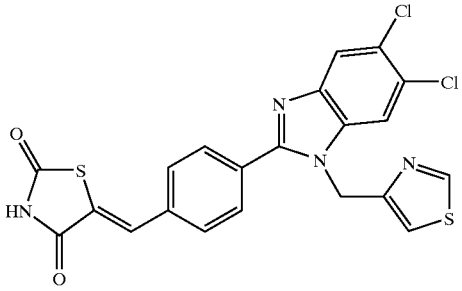

5,6-dichloro2-(4-formylphenyl)-1-(thiazol-4-ylmethyl)benzimidazole was prepared from 5,6-dichloro-2-(4-formylphenyl)benzimidazole obtained in Example(138326) and 4-chloromethylthiazole by following General Procedure 3.

General Procedure 1 was then followed to obtain 5,6-dichloro-2-[4-[(2,4-dioxothiazolidin-5-ylidene)methyl]phenyl]-1-(thiazol-4-ylmethyl)benzimidazole.

ESI–MS m/z 487, 485 (M–H)$^-$, $C_{21}H_{12}{}^{35}Cl_2N_4O_2S_2$=486.

Example 28

Preparation of 2-[4-[(2,4-Dioxothiazolidin-5-yl)methyl]phenyl]-5,6-dichlorobenzimidazole

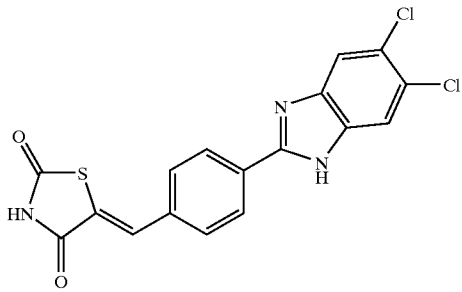

A suspension of 2-[4-[(2,4-dioxothiazolidin-5-ylidene)methyl]phenyl]-5,6-dichlorobenzimidazole (100 mg, 0.256 mmol) and magnesium turnings (125 mg, 5.1 mmol) in methanol (20 mL) was stirred for 40 h at room temperature. Water and hydrochloric acid (1 mol/L) was added, and the mixture was extracted with ethyl acetate. The organic layer was washed washed with water and brine, dried on anhydrous sodium sulfate, and the solvent was removed under reduced pressure. The residue was purified by silica gel column chromatography (10:1 chloroform/methanol) and triturated with ethanol to give 2-[4-[(2,4-dioxothiazolidin-5-yl)methyl]phenyl]-5,6-dichlorobenzimidazole (20 mg, 20%).

$^1$H NMR (400 MHz, DMSO-d$_6$) δ (ppm) 3.19 (dd, J=14.1, 9.0 Hz, 1H), 3.42 (dd, J=14.1, 4.3 Hz, 1H), 4.95 (dd, J=9.0, 4.3 Hz, 1H), 7.40 (d, J=8.2 Hz, 2H), 7.71 (s, 1H), 7.89 (s, 1H), 8.06 (d, J=8.6 Hz, 2H), 12.1 (br s, 1H), 13.2 (br s, 1H); ESI–MS m/z 392, 390 (M–H)$^-$, C$_{17}$H$_{11}$$^{35}$Cl$_2$N$_3$O$_2$S=391.

Example 29

Preparation of 5,6-Dichloro-2-[3-bromo-5-[(2,4-dioxothiazolidin-5-ylidene)methyl]thiophen-2-yl]benzimidazole

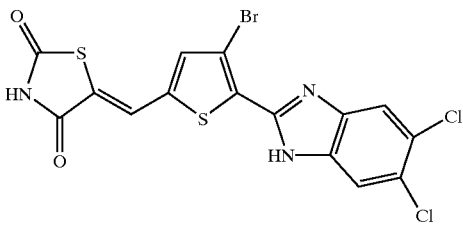

To a mixture of 4-bromothiophene-2-carboxaldehyde (1.91 g, 10.0 mmol) and 2,4-thiazolidinedione (1.40 g, 12.0 mmol) in ethanol (30 mL) was added piperidine (1.0 mL, 10.0 mmol). The reaction mixture was heated at reflux for 3 h, then cooled on an ice-bath, and the precipitated products were collected by filtration. The cake was washed with 40% ethanol and dried to afford 5-(4-bromothiophen-2-ylmethylene)-2,4-thiazolidinedione (2.53 g, 87%).

$^1$H NMR (400 MHz, DMSO-d$_6$) δ (ppm) 7.63 (s, 1H), 7.95 (s, 1H), 8.04 (s, 1H).

To a solution of diisopropylamine (0.46 mL, 3.3 mmol) in tetrahydrofuran (5 mL) was added n-butyllithium (1.6 mol/L in hexanes; 1.9 mL, 3.0 mmol) at 0° C. under nitrogen atmosphere, and the reaction mixture was cooled to –78° C. 5-(4-Bromothiophen-2-ylmethylene)-2,4-thiazolidinedione (290 mg, 1.00 mmol) in tetrahydrofuran (8 mL) was added dropwise followed by the addition of dimethylformamide (0.194 mL, 2.5 mmol), and the mixture was stirred for 10 min. Water and hydrochloric acid (1 mol/L) were added, and the mixture was extracted with ethyl acetate. The organic layer was washed with water and brine, dried on anhydrous sodium sulfate. The solvent was evaporated under reduced pressure, and the residue was triturated with ethyl acetate/hexane to afford 5-(3-bromo-2-folmylthiophen-5-ylmethylene)-2,4-thiazolidinedione (178 mg, 56%).

$^1$H NMR (400 MHz, DMSO-d$_6$) δ (ppm) 7.80 (s, 1H), 7.96 (s, 1H), 9.83 (s, 1H).

5,6-Dichloro-2-[3-bromo-5-[(2,4-dioxothiazolidin-5-ylidene)methyl]thiophen-2-yl]benzimidazole was prepared from 5-(3-bromo-2-folmylthiophen-5-ylmethylene)-2,4-thiazolidinedione and 4,5-dichloro-1,2-phenylenediamine by following General Procedure 2.

$^1$H NMR (400 MHz, DMSO-d$_6$) δ (ppm) 7.78 (s, 1H), 7.80 (br s, 1H), 7.95 (br s, 1H), 7.98 (s, 1H), 12.7 (br s, 1H), 12.9 (br s, 1H); ESI–MS m/z 478, 476, 474 (M+H)$^+$, C$_{15}$H$_6$$^{79}$Br$^{35}$Cl$_2$N$_3$O$_2$S$_2$=473.

Example 30

Preparation of 5,6-Dichloro-2-[3-bromo-5-[(2,4-dioxothiazolidin-5-ylidene)methyl]furan-2-yl]benzimidazole

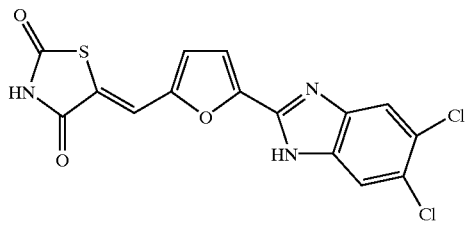

To a solution of 5-bromofuran-2-carboxaldehyde (350 mg, 2.00 mmol) in methanol (15 mL) was added p-toluenesulfonic acid monohydrate (38 mg, 0.20 mmol), and the mixture was heated at reflux for 2 h. The reaction mixture was cooled to room temperature, and aqueous sodium bicarbonate was added. The mixture was extracted with ether, and the organic layer was washed with brine, dried on anhydrous sodium sulfate. The solvent was evaporated under reduced pressure to afford 2-bromo-5-dimethoxymethylfuran (274 mg, 62%).

$^1$H NMR (400 MHz, CDCl$_3$) δ (ppm) 3.32 (s, 6H), 5.35 (s, 1H), 6.25 (d, J=3.1 Hz, 1H), 6.36 (dd, J=3.6, 0.6 Hz, 1H).

To a solution of 2-bromo-5-dimethoxymethylfuran (273 mg, 1.24 mmol) in tetrahydrofuran (7 mL) w e re added n-BuLi (1.6 mol/L in hexane; 1.6 ml, 2.5 mmol) and dimethylformamide (0.25 mL, 3.0 mmol) at –78° C. under nitrogen atmosphere, and the mixture was stirred for 10 min. Water was added and the mixture was extracted with ether. The organic layer was washed with water and brine, dried on anhydrous sodium sulfate, and the solvent was removed under reduced pressure. To the residue were added ethanol (8 mL), 2,4-thiazolidinedione (129 mg, 1.1 mmol), and piperidine (0.092 mL, 0.92 mmol), and the mixture was heated to reflux for 1 h. Water and hydrochloric acid (1 mol/L; 1 mL) were added, and the mixture was extracted with ethyl acetate. The organic layer was washed washed with water and brine, dried on anhydrous sodium sulfate, and the solvent was removed under reduced pressure. The residue was purified by silica gel column chromatography (9:1 chloroform/acetonitrile) gave 5-[(5-dimethoxymethyl-2-furanyl)methylene]-2,4-thiazolidinedione (91 mg, 2 steps 27%).

$^1$H NMR (400 MHz, DMSO-d$_6$) δ (ppm) 3.26 (s, 6H), 5.50 (s, 1H), 6.64 (d, J=3.7 Hz, 1H), 7.01 (d, J=3.4 Hz, 1H), 7.54 (s, 1H), 12.4 (br s, 1H); ESI-MS m/z 268 (M−H)$^−$, C$_{11}$H$_{11}$NO$_5$S=269.

To a solution of 5-[(5-dimethoxymethyl-2-furanyl) methylene]-2,4-thiazolidinedione (87 mg, 0.32 mmol) in tetrahydrofuran (5 mL) was added hydrochloric acid (1 mol/L; 0.4 mL), and the mixture was stirred for 1.5 h at room temperature. Water was added and the precipitated product was collected by filtration to afford 5-[(4-formylfuranyl) methylene]-2,4-thazolidinedione (40 mg, 56%).

$^1$H NMR (400 MHz, DMSO-d$_6$) δ (ppm) 7.21 (d, J=4.0 Hz, 1H), 7.63 (d, J=4.0 Hz, 1H), 7.65 (s, 1H), 9.64 (s, 1H), 12.6 (br s, 1H); ESI-MS m/z 222 (M−H)$^−$, C$_9$H$_5$NO$_4$S=223.

5,6-Dichloro-2-[5-[(2,4-dioxothiazolidin-5-ylidene) methyl]furan-2-yl]benzimidazole was prepared from 5-[(4-formylfuranyl)methylene]-2,4-thazolidinedione and 4,5-dichloro-1,2-phenylenediamine by following General Procedure 2 (48% yield).

$^1$H NMR (400 MHz, DMSO-d$_6$) δ (ppm) 7.24 (d, J=3.9 Hz, 1H), 7.43 (d, J=3.9 Hz, 1H), 7.63 (s, 1H), 7.76 (br s, 1H), 7.96 (br s, 1H), 12.5 (br s, 1H), 13.2 (br s, 1H); ESI-MS m/z 380, 378 (M−H)$^−$, C$_{15}$H$_7$$^{35}$Cl$_2$N$_3$O$_3$S=379.

Example 31

Preparation of 2-[3-Bromo-2-[(2,4-dioxothiazolidin-5-ylidene)methyl]thiophen-5-yl]-5,6-dichlorobenzimidazole

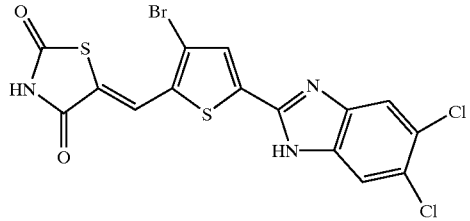

2-(4-Bromothiophen-2-yl)-5,6-dichlorobenzimidazole was prepared from 4-bromo-2-thiophenecarboxaldehyde and 4,5-dichloro-1,2-phenylenediamine by following General Procedure 2.

$^1$H NMR (400 MHz, DMSO-d$_6$) δ (ppm) 7.82 (br s, 2H), 7.83 (d, J=1.6 Hz, 1H), 7.87 (d, J=1.6 Hz, 1H), 13.3 (br s, 1H); ESI-MS m/z 349, 347, 345 (M−H)$^−$, C$_{11}$H$_5$$^{79}$Br$^{35}$Cl$_2$N$_2$S=346.

To a solution of diisopropylamine (0.67 mL, 4.8 mmol) in tetrahydrofuran (6 mL) was added n-butyllithium (1.6 mol/L in hexanes; 2.7 mL, 4.3 mmol) at 0° C. under nitrogen atmosphere, and the reaction mixture was cooled to −78° C. 2-(4-Bromothiophen-2-yl)-5,6-dichlorobenzimidazole (500 mg, 1.44 mmol) in tetrahydrofuran (14 mL) was added dropwise followed by the addition of dimethylformamide (0.33 mL, 4.3 mmol), and the mixture was stirred for 30 min. Water and hydrochloric acid (1 mol/L) were added, and the mixture was extracted with ethyl acetate. The organic layer was washed with water and brine, dried on anhydrous sodium sulfate. The solvent was removed under reduced pressure, and the residue was triturated with ethyl acetate to afford 2-(3-bromo-2-formylthiophen-5-yl)-5,6-dichlorobenzimidazole (296 mg, 55%).

$^1$H NMR (400 MHz, DMSO-d$_6$) δ (ppm) 7.90 (br s, 2H), 7.99 (s, 1H), 9.86 (s, 1H), 13.6 (br s, 1H); ESI-MS m/z 377, 375, 373 (M−H)$^−$, C$_{12}$H$_5$$^{79}$Br$^{35}$Cl$_2$N$_2$OS=344.

General Procedure 1 was then followed to obtain 2-[3-Bromo-2-[(2,4-dioxothiazolidin-5-ylidene)methyl] thiophen-5-yl]-5,6-dichlorobenzimidazole.

$^1$H NMR (400 MHz, DMSO-d$_6$) δ (ppm) 7.71 (s, 1H), 7.85 (br s, 2H), 7.98 (s, 1H), 12.8 (br s, 1H), 13.5 (br s, 1H); ESI-MS m/z 476, 474, 472 (M−H)$^−$, C$_{15}$H$_6$$^{79}$Br$^{35}$Cl$_2$N$_3$O$_2$S$_2$=473.

Example 32

Preparation of 5,6-Dichloro-2-[2-[(2,4-dioxothiazolidin-5-ylidene)methyl]thiophen-5-5-yl] benzimidazole

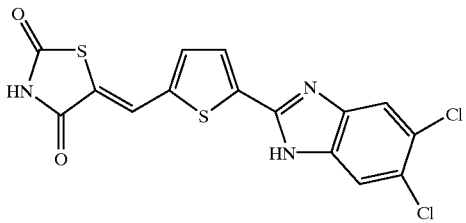

2-(2-Bromothiophen-5-yl)-5,6-dichlorobenzimidazole was obtained from 5-bromo-2-thiophenecarboxaldehyde and 4,5-dichloro-1,2-phenylenediamine by following General Procedure 2.

$^1$H NMR (400 MHz, DMSO-d$_6$) δ (ppm) 7.34 (d, J=3.9 Hz, 1H), 7.65 (d, J=3.9 Hz, 1H), 7.79 (br s, 2H), 13.3 (br s, 1H); ESI-MS m/z 349, 347, 345 (M−H)$^−$, C$_{11}$H$_5$$^{79}$Br$^{35}$Cl$_2$N$_2$S=346.

To a solution of 2-(2-bromothiophen-5-yl)-5,6-dichlorobenzimidazole (100 mg, 0.287 mmol) in tetrahydrofuran (6 mL) was added sodium hydryde (60% oil dispersion; 14 mg, 0.35 mmol) at 0° C. under nitrogen atmosphere. After cooling to −78° C., n-butyllithium (1.6 mol/L in hexane; 0.36 mL, 0.57 mmol), dimethylformamide (0.085 mL, 1.1 mmol) were added, and the mixture was stirred for 10 min. Water was added, and the mixture was extracted with ethyl acetate. The organic layer was washed with water and brine and dried on anhydrous sodium sulfate. The solvent was evaporated under reduced pressure, and the residue was purified by silica gel column chromatography (19:1 to 9:1 chloroform/acetonitrle) to afford 2-(2-formylthiophen-5-yl)-5,6-dichlorobenzimidazole (36 mg, 42%).

$^1$H NMR (400 MHz, DMSO-d$_6$) δ (ppm) 7.80 (br s, 1H), 7.95 (br s, 1H), 7.97 (dd, J=3.9, 1.2 Hz, 1H), 8.07 (dd, J=3.9, 1.2 Hz, 1H), 9.94 (d, J=1.2 Hz, 1H), 13.6 (br s, 2H); ESI-MS m/z 297, 295 (M−H)$^−$, C$_{12}$H$_6$$^{35}$Cl$_2$N$_2$OS=296.

General Procedure 1 was then followed to obtain 5,6-dichloro-2-[2-[(2,4-dioxothiazolidin-5-ylidene)methyl] thiophen-5-yl]benzimidazole.

$^1$H NMR (400 MHz, DMSO-d$_6$) δ (ppm) 7.63 (d, J=3.9 Hz, 1H), 7.75 (br s, 1H), 7.89 (d, J=3.9 Hz, 1H), 7.90 (s, 1H), 8.20 (br s, 1H), 12.3 (br s, 1H), 13.5 (br s, 1H); ESI-MS m/z 396, 394 (M−H)$^−$, C$_{15}$H$_7$$^{35}$Cl$_2$N$_3$O$_2$S$_2$=395.

Example 33

Preparation of 2-[2-[(2,4-Dioxothiazolidin-5-ylidene)methyl]-1-methylpyrrol-5-yl]-5,6-dichlorobenzimidazole

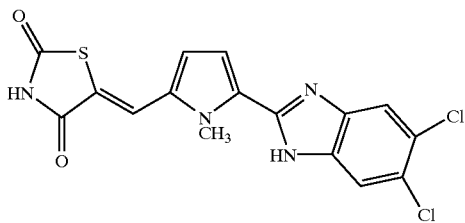

2-(1-Methylpyrrol-2-yl)-5,6-dichlorobenzimidazole was prepared from 1-methyl-2-pyrrolecarboxaldehyde and 4,5-dichloro-1,2-phenylenediamine by following General Procedure 2.

$^1$H NMR (400 MHz, DMSO-d$_6$) δ (ppm) 4.02 (s, 3H), 6.13 (dd, J=3.9, 2.7 Hz, 1H), 6.88 (dd, J=3.9, 2.0 Hz, 1H), 7.00 (t, J=2.0 Hz, 1H), 7.58 (s, 1H), 7.79 (s, 1H), 12.7 (br s, 1H).

To a solution of 2-(1-methylpyrrol-2-yl)-5,6-dichlorobenzimidazole (65 mg, 0.24 mmol) in dimethylformamide (2 mL) was added phosphorus oxychloride (0.067 mL, 0.72 mmol), and the mixture was stirred at room temperature for 24 h. Water and aqueous sodium hydroxide (1.0 mol/L) were added, and the mixture was extracted with ethyl acetate. The organic layer was washed with water and brine and dried on anhydrous sodium sulfate. The solvent was removed under reduced pressure to afford 2-(2-formyl-1-methylpyrrol-5-yl)-5,6-dichlorobenzimidazole (50 mg, 71%).

$^1$H NMR (400 MHz, DMSO-d$_6$) δ (ppm) 4.36 (s, 3H), 7.02 (d, J=4.3 Hz, 1H), 7.14 (d, J=4.3 Hz, 1H), 7.72 (br s, 1H), 7.96 (br s, 1H), 9.65 (s, 1H), 13.2 (br s, 1H); ESI-MS m/z 294, 292 (M–H)$^-$, C$_{13}$H$_9$$^{35}$Cl$_2$N$_3$O=293.

General Procedure 1 was then followed to afford 2-[2-[(2,4-dioxothiazolidin-5-ylidene)methyl]-1-methylpyrrol-5-yl]-5,6-dichlorobenzimidazole.

$^1$H NMR (400 MHz, DMSO-d$_6$) δ (ppm) 4.24 (s, 3H), 6.61 (d, J=4.3 Hz, 1H), 7.12 (d, J=4.3 Hz, 1H), 7.66 (s, 1H), 7.68 (s, 1H), 7.89 (s, 1H), 12.4 (br s, 1H), 13.1 (br s, 1H); ESI-MS m/z 393, 391 (M–H)$^-$, C$_{16}$H$_{10}$$^{35}$Cl$_2$N$_4$O$_2$S=392.

Example 34

Preparation of 2-[4-(2,4-Dioxothiazolidin-5-ylidenemethyl)phenyl]benzothiazole

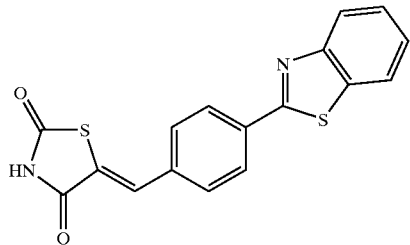

To a suspension of 5-(4-formylbenzylidene)-2,4-thiazolidinedione (50 mg, 0.21 mmol) and 2-aminothiophenol (0.025 mL, 0.23 mmol) in ethanol (7 mL) was heated to reflux for 10 h. 1,4-Benzoquinone (24 mg, 0.22 mmol) was added, and the mixture was heated additional 1 h. The mixture was cooled to room temperature, ether (3 mL) was added, and the precipitated product was collected by filtration to afford 2-[4-(2,4-dioxothiazolidin-5-ylidenemethyl)phenyl]benzothiazole (53 mg, 75%).

$^1$H NMR (400 MHz, DMSO-d$_6$) δ (ppm) 7.45 (ddd, J=8.2, 7.0, 1.2 Hz, 1H), 7.53 (td, J=7.0, 1.2 Hz, 1H), 7.74 (d, J=8.6 Hz, 2H), 7.81 (s, 1H), 8.05 (d, J=7.8 Hz, 1H), 8.14 (d, J=8.2 Hz, 1H), 8.19 (d, J=8.6 Hz, 2H), 12.7 (br s, 1H); ESI-MS m/z 337 (M–H)$^-$, C$_{17}$H$_{10}$N$_2$O$_2$S$_2$=338.

Example 35

Preparation of 5,6-Dichloro-2-[2-[(2,4-dioxothiazolidin-5-ylidene)methyl]pyridin-5-yl]benzimidazole

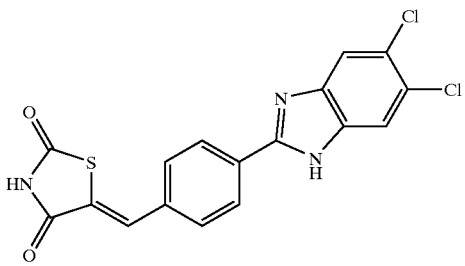

To a solution of 2,5-dibromopyridine (2.37 g, 10.0 mmol) in tetrahydrofuran (15 mL) was added isopropylmagnesium chloride (2 mol/L in tetrahydrofuran; 5.0 mL, 10 mmol) under nitrogen atmosphere, and the mixture was stirred at room temperature for 1 h. Dimethylformamide (1.6 mL, 20 mmol) was added, and the mixture was stirred for additional 15 min. Water was added, and the mixture was extracted with ethyl acetate twice. The organic layer was washed with brine and dried on anhydrous sodium sulfate. The solvent was evaporated under reduced pressure, and the residue was purified by silica gel column chromatography (2:1 hexane/ethyl acetate) to afford 2-bromo-5-pyridinecarboxaldehyde (1.23 g, 66%).

$^1$H NMR (400 MHz, CDCl$_3$) δ (ppm) 7.65 (d, J=8.2 Hz, 1H), 7.99 (dd, J=8.2, 2.3 Hz, 1H), 8.79 (d, J=2.3 Hz, 1H), 10.1 (s, 1H).

To a solution of 2-bromo-5-pyridinecarboxaldehyde (1.02 g, 5.48 mmol) in methanol (100 mL) was added p-toluenesulfonic acid hydrate (1.05 g, 5.53 mmol), and the mixture was heated at reflux for 1.5 h. Diluted aqueous sodium bicarbonate was added, and the mixture was extracted with ethyl acetate twice. The organic layer was washed with brine and dried on anhydrous sodium sulfate. The solvent was evaporated under reduced pressure to afford 2-bromo-5-dimethoxymethylpyridine (1.19 g, 94%) as an oil.

$^1$H NMR (400 MHz, CDCl$_3$) δ (ppm) 3.28 (s, 6H), 5.39 (s, 1H), 7.45 (d, J=8.2 Hz, 1H), 7.59 (dd, J=8.2, 2.3 Hz, 1H), 8.39 (d, J=2.7 Hz, 1H).

To a solution of 2-bromo-5-dimethoxymethylpyridine (1.19 g, 5.13 mmol) in tetrahydrofuran (8 mL) was added isopropylmagnesium chloride (2 mol/L in tetrahydrofuran; 4.2 mL, 8.4 mmol) under nitrogen atmosphere, and the mixture was stirred at room temperature for 3 h. Dimethylformamide (0.774 mL, 10.3 mmol) was added, and the mixture was stirred for additional 10 min. Water was added, and the mixture was extracted with ethyl acetate twice. The organic layer was washed with brine and dried on anhydrous sodium sulfate. The solvent was evaporated under reduced pressure, and the residue was purified by silica gel column chromatography (5:1 to 3:1 hexane/ethyl acetate) to afford 5-dimethoxymethyl-2-pyridinecarboxaldehyde (413 mg, 44%).

¹H NMR (400 MHz, CDCl₃) δ (ppm) 3.32 (s, 6H), 5.50 (s, 1H), 7.9–8.0 (m, 2H), 8.82 (s, 1H), 10.1 (s, 1H).

To a mixture of 5-dimethoxymethyl-2-pyridinecarboxaldehyde (192 mg, 1.06 mmol), 2,4-thiazolidinedione (149 mg, 1.27 mmol) in ethanol (5 mL) was added piperidine (0.11 mL, 1.1 mmol), and the mixture was heated to reflux for 2 h. Hydrochloric acid (1 mol/L, 2 mL) was added, and the mixture was extracted with ethyl acetate. The organic layer was washed with brine and dried on anhydrous sodium sulfate. The solvent was evaporated under reduced pressure. To the residue were added tetrahydrofuran (10 mL) and hydrochloric acid (1 mol/L, 1.2 mL), and the mixture was stirred at room temperature for 14 h. Water was added and the precipitated product was collected by filtration to afford 5-(5-formylpyridin-2-ylmethylene)-2,4-dioxothiazolidinedione (169 mg, 68%).

General Procedure 2 was then followed to obtain 5,6-dichloro-2-[2-[(2,4-dioxothiazolidin-5-ylidene)methyl]pyridin-5-yl]benzimidazole.

¹H NMR (400 MHz, DMSO-d₆) δ (ppm) 7.78 (br s, 1H), 7.82 (s, 1H), 7.95 (br s, 1H), 7.96 (d, J=8.2 Hz, 1H), 8.52 (dd, J=8.2, 2.0 Hz, 1H), 9.39 (s, 1H), 12.5 (br s, 1H), 13.5 (br s, 1H); ESI-MS m/z 391, 389 (M–H)⁻, $C_{16}H_8{}^{35}Cl_2N_4O_2S$=390.

Example 36

Preparation of 5,6-Dichloro-2-[5-[(2,4-dioxothiazolidin-5-ylidene)methyl]pyridin-2-yl]benzimidazole

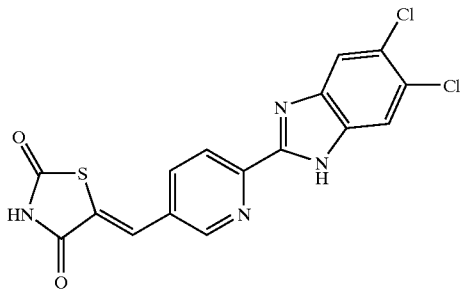

A mixture of 5-dimethoxymethyl-2-pyridinecarboxaldehyde obtained in Example 35 (197 mg, 1.09 mmol), 4,5-diamino-1,2-phenylenediamine (192 mg, 1.09 mmol) and 1,4-benzoquinone (117 mg, 1.09 mmol) in methanol (10 mL) was heated to reflux for 1 h. The solvent was removed under reduced pressure. To the residue were added tetrahydrofuran (10 mL) and hydrochloric acid (1 mol/L, 1.2 mL), and the mixture was stirred at room temperature for 14 h. Water was added, and the mixture was extracted with ethyl acetate. The organic layer was washed with brine and dried on anhydrous sodium sulfate. The solvent was evaporated under reduced pressure, and the residue was triturated with ether to afford 2-(5-formylpyridin-2-yl)-5,6-dichlorobenzimidazole (225 mg, 71%).

¹H NMR (400 MHz, DMSO-d₆) δ (ppm) 7.74 (br s, 1H), 8.00 (br s, 1H), 8.39 (dd, J=8.2, 1.6 Hz, 1H), 8.44 (d, J=7.8 Hz, 1H), 9.19 (s, 1H), 10.1 (s, 1H), 12.8 (br s, 1H); ESI-MS m/z 292, 290 (M–H)⁻ $C_{13}H_7{}^{35}Cl_2N_3O$=291.

General Procedure 1 was then followed to obtain 5,6-dichloro-2-[5-[(2,4-dioxothiazolidin-5-ylidene)methyl]pyridin-2-yl]benzimidazole.

¹H NMR (400 MHz, DMSO-d₆) δ (ppm) 7.67 (s, 1H), 7.82 (s, 1H), 7.99 (s, 1H), 8.10 (dd, J=8.6, 2.3 Hz, 1H), 8.37 (d, J=8.6 Hz, 1H), 8.96 (d, J=2.0 Hz, 1H), 12.8 (br s, 1H), 13.5 (s, 1H); ESI-MS m/z 391, 389 (M–H)⁻, $C_{16}H_8{}^{35}Cl_2N_4O_2S$=390.

Example 37

Preparation of 5,6-Dichloro-2-[4-[2,4-dioxothiazolidin-5-ylidene)methyl]-3-fluorophenyl]benzimidazole

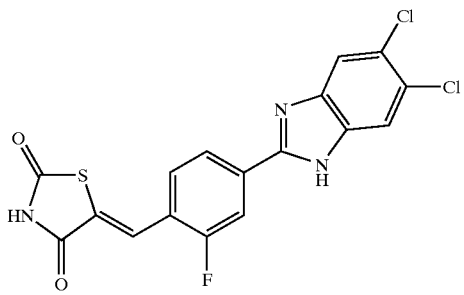

To a solution of 4-bromo-2-fluorobenzaldehyde (3.97 g, 18.8 mmol) in methanol (200 mL) was added p-toluenesulfonic acid monohydrate (357 mg, 1.88 mmol), and the mixture was heated to reflux for 4 h. Aqueous sodium carbonate (1 mol/L; 2 mL) was added, and the mixture was concentrated to a volume of ca. 50 mL and extracted with ether. The organic layer was washed with brine and dried on anhydrous sodium sulfate. The solvent was removed under reduced pressure to afford 4-bromo-1-dimethoxymethyl-2-fluorobenzene (4.56 g, 97%).

¹H NMR (400 MHz, CDCl₃) δ (ppm) 3.33 (s, 6H), 5.52 (s, 1H), 7.21 (dd, J=9.6, 1.8 Hz, 1H), 7.28 (dd, J 8.4, 1.8 Hz, 1H), 7.41 (t, J=7.8 Hz, 1H).

To a solution of 4-bromo-1-dimethoxymethyl-2-fluorobenzene (4.53 g, 18.2 mmol) in 1 tetrahydrofuran (50 mL) were added n-butyllithium (1.6 mol/L in hexanes; 15 mL) and dimethylformamide (2.1 mL, 27 mmol) sequentially at −78° C. under nitrogen atmosphere, and the mixture was stirred for 15 min. Water was added, and the mixture was extracted twice with ether. The organic layer was combined, washed with brine and dried on anhydrous sodium sulfate. The solvent was removed under reduced pressure, and the residue was purified by column chromatography (6:1 Hexane/ethyl acetate) to afford 4-dimethoxymethyl-3-fluorobenzaldehyde (2.26 g, 63%).

¹H NMR (400 MHz, CDCl₃) δ (ppm) 3.36 (s, 6H), 5.61 (s, 1H), 7.53 (dd, J=9.8, 1.6 Hz, 1H), 7.65 (dd, J=7.8, 1.6 Hz, 1H), 7.73 (t, J=7.8 Hz, 1H), 9.95 (d, J=2.0 Hz, 1H).

A mixture of 4-dimethoxymethyl-3-fluorobenzaldehyde (321 mg, 1.62 mmol), 4,5-dichloro-1,2-phenylenediamine (283 mg, 1.60 mg) and 1,4-benzoquinone (173 mg, 1.60 mmol) in methanol (10 mL) was heated to reflux for 2 h. The solvent was removed under reduced pressure. To the residue were added tetrahydrofuran (15 mL) and hydrochloric acid (1 mol/L; 1.6 mL), and the mixture was stirred at room temperature for 16 h. Water was added and the precipitated products were collected by filtration, followed by trituration with ether to afford 5,6-dichloro-2-(3-fluoro-4-formylphenyl)benzimidazole (132 mg, 26%).

$^1$H NMR (400 MHz, DMSO-d$_6$) δ (ppm) 7.89 (br s, 2H), 7.98 (t, J=7.8 Hz, 1H), 8.06 (dd, J=11.2, 1.2 Hz, 1H), 8.11 (dd, J=7.8 1.2 Hz, 1H), 10.2 (s, 1H); ESI-MS m/z 309, 307 (M-H)$^-$ C$_{14}$H$_7$$^{35}$Cl$_2$N$_2$O=308.

General Procedure 1 was then followed to obtain 5,6-dichloro-2-[4-[2,4-dioxothiazolidin-5-ylidene)methyl]-3-fluorophenyl]benzimidazole.

$^1$H NMR (400 MHz, DMSO-d$_6$) δ (ppm) 7.68 (t, J=8.2 Hz, 1H), 7.70 (s, 1H), 7.78 (br s, 1H), 7.94 (br s, 1H), 8.02 (d, J=11.7 Hz, 1H), 8.09 (d, J=8.6 Hz, 1H), 12.8 (br s, 1H), 13.4 (br s, 1H); ESI-MS m/z 408, 406 (M-H)$^-$, C$_{17}$H$_8$$^{35}$Cl$_2$FN$_3$O$_2$S=407.

Example 38

Preparation of 5,6-Dichloro-2-[4-[(2,4-dioxothiazolidin-5-ylidene)methyl]-2-fluorophenyl]benzimidazole

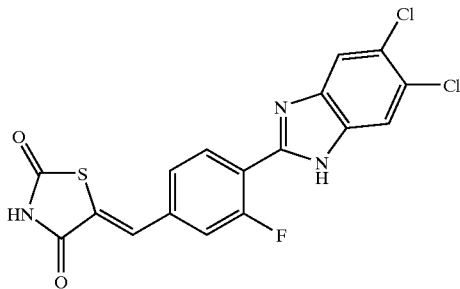

To a mixture of 4-dimethoxymethyl-3-fluorobenzaldehyde obtained in Example 37 (1.12 g, 5.66 mmol) and 2,4-thiazolidindione (795 mg, 6.79 mmol) in ethanol (20 mL) was added piperidine (0.68 mL, 6.8 mmol), and the mixture was heated to reflux for 13 h. Hydrochloric acid (1 mol/L) was added, and the mixture was extracted with ethyl acetate. The organic layer was combined, washed with brine, dried on anhydrous sodium sulfate, and concentrated under reduced pressure. To the residue were added tetrahydrofuran (25 mL) and hydrchloric acid (1 mol/L; 5 mL), and the mixture was stirred at room temperature for 20 h. Water was added, and the precipitated products were collected by filtration to afford 3-fluoro-4-formylbenzylidene-2,4-thiazolidinedione (696 mg, 49%).

$^1$H NMR (400 MHz, DMSO-d$_6$) δ (ppm) 7.53 (d, J=7.8 Hz, 1H), 7.60 (dd, J=11.7, 1.2 Hz, 1H), 7.79 (s, 1H), 7.92 (t, J=7.8 Hz, 1H), 10.2 (s, 1H), 12.8 (br s, 1H); ESI-MS m/z 250 (M-H)$^-$ C$_{11}$H$_6$FNO$_3$=251.

General Procedure 2 was then followed to obtain 5,6-dichloro-2-[4-[(2,4-dioxothiazolidin-5-ylidene)methyl]-2-fluorophenyl]benzimidazole (58 mg, 71%).

$^1$H NMR (400 MHz, DMSO-d$_6$) δ (ppm) 7.54 (d, J=8.6 Hz, 1H), 7.66 (d, J=12.5 Hz, 1H), 7.79 (s, 1H), 7.85 (br s, 2H), 8.30 (t, J=8.2 Hz, 1H), 12.7 (br s, 1H), 12.9 (br s, 1H); ESI-MS m/z 408, 406 (M-H)$^-$, C$_{17}$H$_8$$^{35}$Cl$_2$FN$_3$O$_2$S=407.

Example 39

Preparation of 5,6-Dichloro-2-[4-[(2,4-dioxothiazolidin-5-ylidene)methyl]naphth-1-yl]benzimidazole

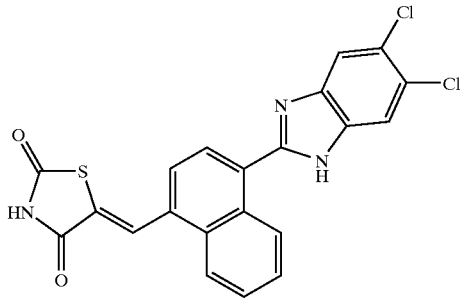

To a solution of 1,4-dibromonaphthalene (1.00 g, 3.50 mmol) in tetrahydrofuran (15 mL) were added n-butyllithium (1.6 mol/L; 3.1 mL) and dimethylformamide (0.54 mL, 7.0 mmol) sequentially at −78° C. under nitrogen atmosphere, and the mixture was stirred for 15 min. Water was added, and the mixture was extracted with ethyl acetate. The organic layer was combined, washed with brine and dried on anhydrous sodium sulfate. The solvent was removed under reduced pressure, and the residue was purified by column chromatography (8:1 hexane/ethyl acetate) to afford 4-bromo-1-naphthalenecarboxaldehyde (458 mg, 56%).

$^1$H NMR (400 MHz, CDCl$_3$) δ (ppm) 7.6–7.8 (m, 2H), 7.78 (d, J=7.8 Hz, 1H), 7.94 (d, J=7.8 Hz, 1H), 8.34 (dd, J=8.2, 1.6 Hz, 1H), 9.25 (dd, J=8.2, 1.6 Hz, 1H), 10.3 (s, 1H).

General Procedure 2 was followed to obtain 5,6-dichloro-2-(4-bromo-1-naphthyl)benzimidazole.

$^1$H NMR (400 MHz, DMSO-d$_6$) δ (ppm) 7.8–7.9 (m, 2H), 7.87 (d, J=7.8 Hz, 1H), 7.91 (br s, 2H), 8.07 (d, J=7.8 Hz, 1H), 8.25 (d, J=7.0 Hz, 1H), 9.04 (d, J=8.2 Hz, 1H), 13.3 (br s, 1H); ESI-MS m/z 393, 391, 389 (M-H)$^-$ C$_{17}$H$_9$Br$^{35}$Cl$_2$N$_2$=390.

To a solution of 5,6-dichloro-2-(4-bromo-1-naphthyl)benzimidazole (160 mg, 0.408 mmol) in tetrahydrofuran (6 mL) were added n-butyllithium (1.6 mol/L; 0.64 mL) and dimethylformamide (0.077 mL, 1.0 mmol) sequentially at −78° C. under nitrogen atmosphere, and the mixture was stirred for 15 min. Water was added, and the mixture was extracted with ethyl acetate. The organic layer was combined, washed with brine and dried on anhydrous sodium sulfate. The solvent was removed under reduced pressure, and the residue was purified by column chromatography (2:1 hexane/ethyl acetate) to afford 5,6-dichloro-2-(4-formyl-1-naphthyl)benzimidazole (72 mg, 52%).

$^1$H NMR (400 MHz, DMSO-d$_6$) δ (ppm) 7.7–7.9 (m, 2H), 7.96 (br s, 2H), 8.17 (d, J=7.4 Hz, 1H), 8.31 (d, J=7.4 Hz, 1H), 9.04 (dd, J=8.6, 1.6 Hz, 1H), 9.23 (d, J=8.6 Hz, 1H), 10.5 (s, 1H), 13.4 (br s, 1H); ESI-MS m/z 341, 339 (M-H)$^-$ C$_{18}$H$_{10}$$^{35}$Cl$_2$N$_2$O=340.

General Procedure 1 was then followed to obtain 5,6-dichloro-2-[4-[(2,4-dioxothiazolidin-5-ylidene)methyl]naphth-1-yl]benzimidazole.

$^1$H NMR (400 MHz, DMSO-d$_6$) δ (ppm) 7.6–7.7 (m, 2H), 7.83 (d, J=7.8 Hz, 1H), 7.90 (br s, 2H), 7.99 (s, 1H), 8.03 (d, J=7.8 Hz, 1H), 8.21 (d, J=9.4 Hz, 1H), 9.08 (d, J=9.7 Hz, 1H); ESI-MS m/z 440, 438 (M-H)$^-$, C$_{21}$H$_{11}$$^{35}$Cl$_2$N$_3$O$_2$S=439.

Example 40

Preparation of 5,6-Dichloro-2-[6-[(2,4-dioxothiazolidin-5-ylidene)methyl]naphth-2-yl]benzimidazole

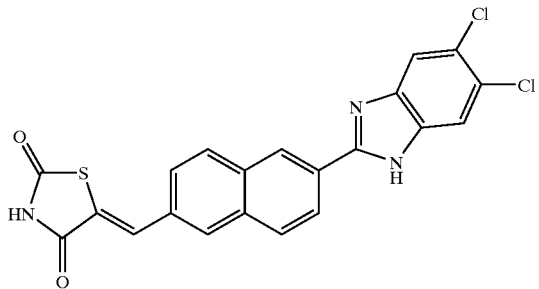

5,6-dichloro-2-[6-[(2,4-dioxothiazolidin-5-ylidene)methyl]naphth-2-yl]benzimidazole was obtained in a similar manner to Example 39 in 4 steps from 2,6-dibromonaphthalene.

$^1$H NMR (400 MHz, DMSO-d$_6$) δ (ppm) 7.72 (d, J=8.6 Hz, 1H), 7.76 (br s, 1H), 7.89 (s, 1H), 7.93 (br s, 1H), 8.11 (d, J=8.6 Hz, 1H), 8.15 (d, J=8.6 Hz, 1H), 8.18 (s, 1H), 8.29 (d, J=8.6 Hz, 1H), 8.71 (s, 1H), 12.6 (br s, 1H), 13.4 (br s, 1H); ESI-MS m/z 440, 438 (M−H)$^-$, C$_{21}$H$_{11}$$^{35}$Cl$_2$N$_3$O$_2$S=439.

Example 41

Preparation of 5,6-Dichloro-2-[2,5-dimethyl-6-[(2,4-dioxothiazolidin-5-ylidene)methyl]pyridin-3-yl]benzimidazole

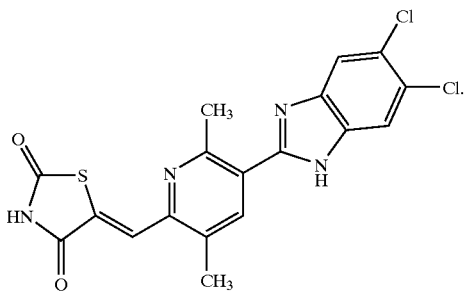

To a solution of 2,5-dibromo-3,6-dimethylpyridine (989 mg, 3.75 mmol) in tetrahydrofuran (6 mL) was added isopropylmagnesium chloride (2 mol/L in tetrahydrofuran; 2.0 mL, 4.0 mmol) under nitrogen atmosphere, and the mixture was stirred at room temperature for 1.5 h. Dimethylformamide (0.58 mL, 7.5 mmol) was added, and the mixture was stirred for additional 10 min. Water was added, and the mixture was extracted with ethyl acetate. The organic layer was washed with brine and dried on anhydrous sodium sulfate. The solvent was evaporated under reduced pressure, and the residue was purified by silica gel column chromatography (7:1 hexane/ethyl acetate) to afford 6-bromo-2,5-dimethyl-3-pyridinecarboxaldehyde (381 mg, 47%).

$^1$H NMR (400 MHz, CDCl$_3$) δ (ppm) 2.40 (s, 3H), 2.79 (s, 3H), 7.85 (s, 1H), 10.3 (s, 1H).

To a solution of 6-bromo-2,5-dimethyl-3-pyridinecarboxaldehyde (378 g, 1.77 mmol) in methanol (25 mL) was added p-toluenesulfonic acid hydrate (342 mg, 1.80 mmol), and the mixture was heated at reflux for 1 h. Diluted aqueous sodium bicarbonate was added, and the mixture was extracted with ethyl acetate. The organic layer was washed with brine and dried on anhydrous sodium sulfate. The solvent was evaporated under reduced pressure to afford 2-bromo-5-dimethoxymethyl-3,6-dimethylpyridine (423 g, 92%).

$^1$H NMR (400 MHz, CDCl$_3$) δ (ppm) 2.32 (s, 3H), 2.48 (s, 3H), 3.27 (s, 6H), 5.37 (s, 1H), 7.62 (S, 1H).

To a solution of 2-bromo-5-dimethoxymethyl-3,6-dimethylpyridine (382 mg, 1.47 mmol) in tetrahydrofuran (6 mL) were added n-butyllithium (1.6 mol/L; 1,4 mL, 2.2 mmol) and dimethylformamide (0.23 mL, 3.0 mmol) sequentially at −78° C. under nitrogen atmosphere, and the mixture was stirred for 40 min. Water was added, and the mixture was extracted with ethyl acetate. The organic layer was combined, washed with brine and dried on anhydrous sodium sulfate. The solvent was removed under reduced pressure, and the residue was purified by column chromatography (6:1 hexane/ethyl acetate) to afford 5-dimethoxymetyl-3,6-dimethyl-2-pyridinecarboxaldehyde (109 mg, 35%).

$^1$H NMR (400 MHz, CDCl$_3$) δ (ppm) 2.60 (s, 6H), 3.30 (s, 6H), 5.45 (s, 1H), 7.73 (s, 1H), 10.1 (s, 1H); ESI-MS m/z 210 (M+H)$^+$ C$_{11}$H$_{15}$NO$_3$=209.

To a mixture of 5-dimethoxymetyl-3,6-dimethyl-2-pyridinecarboxaldehyde (53 mg, 0.25 mmol) and 2,4-thiazolidindione (44 mg, 0.38 mmol) in ethanol (5 mL) was added piperidine (0.038 mL, 0.38 mmol), and the mixture was heated to reflux for 16 h. Hydrochloric acid (1 mol/L; 0.4 mL) and water were added, and the mixture was extracted with ethyl acetate. The organic layer was washed with brine, dried on anhydrous sodium sulfate, and concentrated under reduced pressure. To the residue were added tetrahydrofuran (4 mL) and hydrochloric acid (1 mol/L; 0.5 mL), and the mixture was stirred at room temperature for 7 h. Water was added, and the precipitated products were collected by filtration to afford 5-formyl-3,6-dimethylpyridin-2-ylidene-2,4-thiazolidinedione (43 mg, 66%).

$^1$H NMR (400 MHz, DMSO-d$_6$) δ (ppm) 2.46 (s, 3H), 2.77 (s, 3H), 7.75 (s, 1H), 8.05 (s, 1H), 10.2 (s, 1H), 12.5 (br s, 1H); ESI-MS m/z 261 (M−H)$^-$ C$_{12}$H$_{10}$N$_2$O$_3$S=262.

General Procedure 2 was then followed to obtain 5,6-dichloro-2-[2,5-dimethyl-6-[(2,4-dioxothiazolidin-5-ylidene)methyl]pyridin-3-yl]benzimidazole.

$^1$H NMR (400 MHz, DMSO-d$_6$) δ (ppm) 2.48 (s, 3H), 2.84 (s, 3H), 7.76 (s, 2H), 7.95 (s, 1H), 8.10 (s, 1H), 12.4 (br s, 1H), 13.1 (br s, 1H); ESI-MS m/z 419, 417 (M−H)$^-$, C$_{18}$H$_{12}$$^{35}$Cl$_2$N$_4$O$_2$S=418.

Example 42

Preparation of 2-[3,6-Dimethyl-5-(2,4-dioxothiazolidin-5-ylidenemethyl)pyridin-2-yl]-5,6-dichlorobenzimidazole

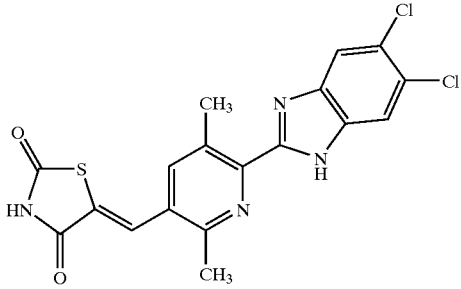

A mixture of 5-dimethoxymetyl-3,6-dimethyl-2-pyridinecarboxaldehyde obtained in Example 41 (57 mg, 0.27 mmol), 4,5-diamino-1,2-phenylenediamine (48 mg, 0.27 mmol) and 1,4-benzoquinone (29 mg, 0.27 mmol) in methanol (5 mL) was heated to reflux for 6 h. The solvent was removed under reduced pressure. To the residue were added tetrahydrofuran (5 mL) and hydrochloric acid (1 mol/L, 0.54 mL), and the mixture was stirred at room temperature for 18 h. The mixture was neutralized by aqueous sodium hydroxide. Water was further added and the precipitated products were collected by filtration followed by trituration with ether to afford 5,6-dichloro-2-(5-formyl-3,6-dimethylpyridin-2-yl)benzimidazole (43 mg, 50%).

$^1$H NMR (400 MHz, DMSO-$d_6$) δ (ppm) 2.81 (s, 3H), 2.84 (s, 3H), 7.74 (s, 1H), 8.0 (s, 11H), 8.14 (s, 1H), 10.2 (s, 1H), 13.1 (br s, 1H); ESI-MS m/z 320, 318 (M-H)$^-$ $C_{15}H_{11}{}^{35}Cl_2N_3O$=319.

General Procedure 1 was then followed to obtain 2-[3,6-dimethyl-5-(2,4-dioxothiazolidin-5-ylidenemethyl)pyridin-2-yl]-5,6-dichlorobenzimidazole.

$^1$H NMR (400 MHz, DMSO-$d_6$) δ (ppm) 2.65 (s, 3H), 2.79 (s, 3H), 7.67 (s, 1H), 7.71 (s, 1H), 7.78 (s, 1H), 7.97 (s, 1H), 12.7 (br s, 1H), 13.0 (br s, 1H); ESI-MS m/z 419, 417 (M-H)$^-$, $C_{18}H_{12}{}^{35}Cl_2N_4O_2S$=418.

Example 43

Preparation of 5,6-Dichloro-2-[2-[(2,4-dioxothiazolidin-5-ylidene)methyl]quinolin-6-yl]benzimidazole

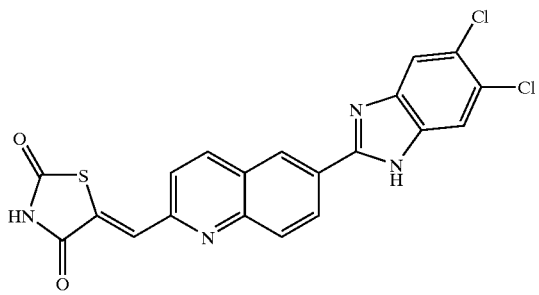

To a solution of 6-bromoquinaldine (111 mg, 0.500 mmol) in 1,4-dioxane (8 mL) was added selenium dioxide (111 mg, 1.00 mmol), and the mixture was heated at 100° C. for 1 h. The reaction mixture was diluted with ethyl acetate, filtered through Celite pad, and concentrated under reduced pressure. To the residue were added methanol (15 mL) and p-toluenesulfonic acid monohydrate (99 mg, 0.52 mmol), and the mixture was heated to reflux for 1.5 h. Diluted aqueous sodium hydroxide was added, and the mixture was extracted with ethyl acetate. The organic layer was washed with brine and dried on anhydrous sodium sulfate. The solvent was evaporated under reduced pressure to afford 6-bromo-2-(dimethoxymethyl)quinoline (127 mg, 90%).

$^1$H NMR (400 MHz, CDCl$_3$) δ (ppm) 3.43 (s, 6H), 5.44 (s, 1H), 7.65 (d, J=8.6 Hz, 1H), 7.75 (dd, J=9.0, 2.0 Hz, 1H), 7.96 (d, J=2.0 Hz, 1H), 7.99 (d, J=9.0 Hz, 1H), 8.09 (d, J=8.6 Hz, 1H); ESI-MS m/z 284, 282 (M+H)$^+$ $C_{12}H_{12}BrNO_2$=281.

To a solution of 6-bromo-2-(dimethoxymethyl)quinoline (1.11 g, 3.94 mmol) in tetrahydrofuran (20 mL) were added n-butyllithium (1.6 mol/L; 3.7 mL, 5.9 mmol) and dimethylformamide (0.61 mL, 7.9 mmol) sequentially at −78° C. under nitrogen atmosphere, and the mixture was stirred for 10 min. Water was added, and the mixture was extracted with ethyl acetate. The organic layer was combined, washed with brine and dried on anhydrous sodium sulfate. The solvent was removed under reduced pressure, and the residue was purified by column chromatography (3:1 hexane/ethyl acetate) to afford 2-dimethoxymethyl-6-quinolinecarboxaldehyde (344 mg, 38%).

$^1$H NMR (400 MHz, CDCl$_3$) δ (ppm) 3.46 (s, 6H), 5.47 (s, 1H), 7.75 (d, J=8.6 Hz, 1H), 8.17 (dd, J=9.0, 2.0 Hz, 1H), 8.22 (d, J=9.0 Hz, 1H), 8.32 (s, 1H), 8.33 (s, 1H), 10.2 (s, 1H).

A mixture of 2-dimethoxymethyl-6-quinolinecarboxaldehyde (162 mg, 0.701 mmol), 4,5-diamino-1,2-phenylenediamine (124 mg, 0.701 mmol) and 1,4-benzoquinone (75 mg, 0.70 mmol) in ethanol (5 mL) was heated to reflux for 2 h. The solvent was removed under reduced pressure. To the residue were added tetrahydrofuran (10 mL) and hydrochloric acid (1 mol/L, 2 mL), and the mixture was heated to reflux for 2 h. The mixture was neutralized by aqueous sodium hydroxide. Water was further added and the precipitated products were collected by filtration followed by trituration with ether to afford 5,6-dichloro-2-(2-formylquinoline-6-yl)benzimidazole (139 mg, 58%).

$^1$H NMR (400 MHz, DMSO-$d_6$) δ (ppm) 7.86 (br s, 2H), 8.00 (d, J=8.6 Hz, 1H), 8.32 (d, J=8.6 Hz, 1H), 8.57 (d, J=8.6 Hz, 1H), 8.66 (d, J=8.2 Hz, 1H), 8.83 (s, 1H), 10.1 (s, 1H), 13.6(br s, 1H).

General Procedure 1 was then followed to obtain 5,6-dichloro-2-[2-[(2,4-dioxothiazolidin-5-ylidene)methyl]quinolin-6-yl]benzimidazole.

$^1$H NMR (400 MHz, DMSO-$d_6$) δ (ppm) 7.84 (br s, 2H), 7.94 (s, 1H), 7.96 (d, J=8.6 Hz, 1H), 8.19 (d, J=9.0 Hz, 1H), 8.51 (d, J=9.0, 1H), 8.53 (d, J=9.0 Hz, 1H), 12.5 (br s, 1H); ESI-MS m/z 441, 439 (M-H)$^-$, $C_{20}H_{10}{}^{35}Cl_2N_4O_2S$=440.

Example 44

Preparation of 5,6-Dichloro-2-[6-[(2,4-dioxothiazolidin-5-ylidene)methyl]quinolin-2-yl]benzimidazole

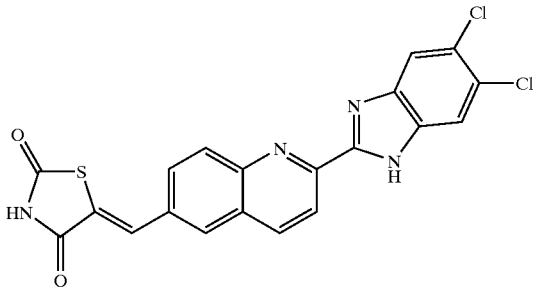

To a mixture of 2-dimethoxymethyl-6-quinolinecarboxaldehyde obtained in Example 43 (181 mg, 0.783 mmol), 2,4-thiazolidinedione (137 mg, 1.17 mmol) in ethanol (5 mL) was added piperidine (0.117 mL, 1.17 mmol), and the mixture was heated to reflux for 26 h. Hydrochloric acid (1 mol/L, 1.2 mL) and water were added, and the mixture was extracted with ethyl acetate. The organic layer was washed with brine and dried on anhydrous sodium sulfate. The solvent was evaporated under reduced pressure. To the residue were added tetrahydrofuran (10 mL) and hydrochloric acid (1 mol/L, 2 mL), and the mixture was heated to reflux for 1 h. The mixture was neutralized by aqueous sodium hydroxide. Water was further added and the precipitated products were collected by filtration followed by trituration with ether to afford 2-formylquinolin-6-ylmethylene-2,4-thiazolidindione (80 mg, 36%).

$^1$H NMR (400 MHz, DMSO-$d_6$) δ (ppm) 7.94 (s, 1H), 7.99 (d, J=8.6 Hz, 1H), 8.03 (d, J=8.6 Hz, 1H), 8.27 (d, J=8.6 Hz, 1H), 8.28 (s, 1H), 8.68 (d, J=8.2 Hz, 1H), 10.1 (s, 1H), 12.7 (br s, 1H); ESI–MS m/z 283 (M–H)$^-$, $C_{14}H_8N_2O_2S$=284.

General Procedure 2 was then followed to obtain 5,6-dichloro-2-[6-[(2,4-dioxothiazolidin-5-ylidene)methyl]quinolin-2-yl]benzimidazole.

$^1$H NMR (400 MHz, DMSO-$d_6$) δ (ppm) 7.70 (br s, 1H), 7.88 (s, 1H), 7.93 (dd, J=9.0, 1.6 Hz, 1H), 7.97 (br s, 1H), 8.13 (d, J=9.0 Hz, 1H), 8.17 (s, 1H), 8.37 (d, J=8.6 Hz, 1H), 8.57 (d, J=8.6 Hz, 1H), 12.7 (br s, 1H), 13.4 (br s, 1H); ESI–MS m/z 441, 439 (M–H)$^-$, $C_{20}H_{10}{}^{35}Cl_2N_4O_2S$=440.

Example 45

Preparation of 5,6-Dichloro-2-[5-[(2,4-dioxothiazolidin-5-ylidene)methyl]indol-2-yl]benzimidazole

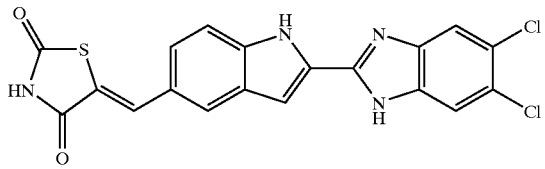

To a solution of indole-5-carboxaldehyde (2.00 g, 13.8 mmol) in dimethylformamide (50 mL) were added sodium hydride (60% oil dispersion; 828 mg, 20.7 mmol) and p-toluenesulfonyl chloride (3.16 g, 16.6 mmol) at 0° C. under nitrogen atmosphere, and the mixture was stirred for 13 h at room temperature. Water was added, and the mixture was extracted with ethyl acetate. The organic layer was washed with brine and dried on anhydrous sodium sulfate. The solvent was evaporated under reduced pressure, and the residue was purified by silica gel column chromatography (5:1 hexane/ethyl acetate) to afford 1-(4-methylphenyl)sulfonylindole-5-carboxaldehyde (2.86 g, 69%).

$^1$H NMR (400 MHz, CDCl$_3$) δ (ppm) 2.32 (s, 3H), 6.75 (d, J=3.5 Hz, 1H), 7.22 (d, J=8.2 Hz, 2H), 7.64 (d, J=3.9 Hz, 1H), 7.76 (d, J=8.6 Hz, 2H), 7.82 (dd, J=8.6, 1.6 Hz, 1H), 8.03 (d, J=1.6 Hz, 1H), 8.08 (d, J=8.6 Hz, 1H), 9.99 (s, 1H).

To a solution of 1-(4-methylphenyl)sulfonylindole-5-carboxaldehyde (2.30 g, 7.69 mmol) in methanol (120 mL) was added p-toluenesulfonic acid monohydrate (146 mg, 0769 mmol), and the mixture was heated to reflux for 2 h. Diluted aqueous sodium hydroxide was added, and the mixture was extracted with ether. The organic layer was washed with brine and dried on anhydrous sodium sulfate. The solvent was evaporated under reduced pressure to afford 5-dimethoxymethyl-1-(4-methylphenyl)sulfonylindole (2.64 g, 99%).

$^1$H NMR (400 MHz, DMSO-$d_6$) δ (ppm) 2.24 (s, 3H), 3.33 (s, 6H), 5.36 (s, 1H), 6.80 (d, J=3.5 Hz, 1H), 7.31 (d, J=7.8 Hz, 3H), 7.56 (s, 1H), 7.76 (d, J=3.5 Hz, 1H), 7.81 (d, J=8.2 Hz, 2H), 7.88 (d, J=8.6 Hz, 1H).

To a solution of 5-dimethoxymethyl-1-(4-methylphenyl)sulfonylindole (2.37 g, 6.87 mmol) in tetrahydrofuran (35 mL) was added n-butyllithium (1.6 mol/L in hexanes; 6.2 mL, 9.9 mmol) at −78° C. under nitrogen atmosphere, and the mixture was stirred for 2 h. Then dimethylformamide (1.1 mL, 14 mmol) was added, and the mixture was stirred for 20 min. Water was added, and the mixture was extracted with ethyl acetate. The organic layer was combined, washed with brine and dried on anhydrous sodium sulfate. The solvent was removed under reduced pressure, and the residue was purified by column chromatography (4:1 hexane/ethyl acetate) followed by trituration with hexane to afford 5-dimethoxymethyl-1-(4-methylphenyl)sulfonylindole-2-carboxaldehyde (1.89 g, 74%).

$^1$H NMR (400 MHz, DMSO-$d_6$) δ (ppm) 2.26 (s, 3H), 3.19 (s, 6H), 5.41 (s, 1H), 7.33 (d, J=8.2 Hz, 2H), 7.54 (dd, J=8.6, 1.6 Hz, 1H), 7.65 (s, 1H), 7.75 (s, 1H), 7.76 (d, J=8.2 Hz, 2H), 8.10 (d, J=8.6 Hz, 1H), 10.3 (s, 1H).

A mixture of 5-dimethoxymethyl-1-(4-methylphenyl)sulfonylindole-2-carboxaldehyde (200 mg, 0.536 mmol), 4,5-diamino-1,2-phenylenediamine (94 mg, 0.54 mmol) and 1,4-benzoquinone (57 mg, 0.54 mmol) in ethanol (6 mL) was heated to reflux for 13 h. The solvent was removed under reduced pressure. To the residue were added tetrahydrofuran (10 mL) and hydrochloric acid (1 mol/L, 0.1 mL), and the mixture was stirred at room temperature for 1 h. Water was further added and the mixture was extracted with ethyl acetate. The organic layer was washed with brine and dried on anhydrous sodium sulfate. The solvent was removed under reduced pressure, and triturated with ether to afford 5,6-dichloro-2-[5-formyl-1-(4-methylphenyl)sulfonylindol-2-yl]benzimidazole (149 mg, 57%).

$^1$H NMR (400 MHz, DMSO-$d_6$) δ (ppm) 2.25 (s, 3H), 7.32 (d, J=8.6 Hz, 2H), 7.45 (s, 1H), 7.74 (d, J=8.6, 2H), 7.94 (d, J=9.0 Hz, 1H), 7.95 (br s, 2H), 8.21 (s, 1H), 8.25 (d, J=9.0 Hz, 1H), 9.99 (s, 1H), 13.5 (br s, 1H); ESI–MS m/z 484, 482 (M–H)$^-$, $C_{23}H_{15}{}^{35}Cl_2N_3O_3S$=483.

General Procedure 1 was then followed to obtain 5,6-dichloro-2-[5-[(2,4-dioxothiazolidin-5-ylidene)methyl]-1-(4-methylphenyl)sulfonylindol-2-yl]benzimidazole.

¹H NMR (400 MHz, DMSO-d₆) δ (ppm) 2.25 (s, 3H), 7.31 (d, J=8.2 Hz, 2H), 7.37 (s, 1H), 7.66 (dd, J=8.6, 1.6 Hz, 1H), 7.70 (d, J=8.6 Hz, 2H), 7.81 (s, 1H), 7.85 (s, 1H), 7.86 (s, 1H), 8.04 (s, 1H), 8.19 (d, J=8.6 Hz, 1H), 12.6 (br s, 1H), 13.5 (br s, 1H); ESI–MS m/z 583, 581 (M–H)⁻, $C_{26}H_{16}{}^{35}Cl_2N_4O_4S_2$=582.

To a suspension of 5,6-dichloro-2-[5-[(2,4-dioxothiazolidin-5-ylidene)methyl]-1-(4-methylphenyl)sulfonylindol-2-yl]benzimidazole (77 mg, 0.13 mmol) in methanol (5 mL) was added aqueous sodium hydroxide (2 mol/L; 1 mL), and the mixture was heated to reflux for 19 h. The reaction mixture was cooled on an ice bath, and pH was adjusted to 7. The precipitated products were collected by filtration followed by trituration with tetrahydrofuran/ethyl acetate to afford 5,6-dichloro-2-[5-[(2,4-dioxothiazolidin-5-ylidene)methyl]indol-2-yl]benzimidazole (10 mg, 18%).

¹H NMR (400 MHz, DMSO-d₆) δ (ppm) 7.32 (s, 1H), 7.40 (d, J=9.0 Hz, 1H), 7.54 (d, J=8.6 Hz, 1H), 7.78 (s, 1H), 7.84 (s, 1H), 7.89 (s, 1H), 7.92 (s, 1H), 12.4 (br s, 2H), 13.4 (br s, 1H); ESI–MS m/z 429, 427 (M–H)⁻, $C_{19}H_{10}{}^{35}Cl_2N_4O_2S$=428.

Example 46

Preparation of 5,6-Dichloro-2-[2-[(2,4-dioxothiazolidin-5-ylidene)methyl]indol-5-yl]benzimidazole

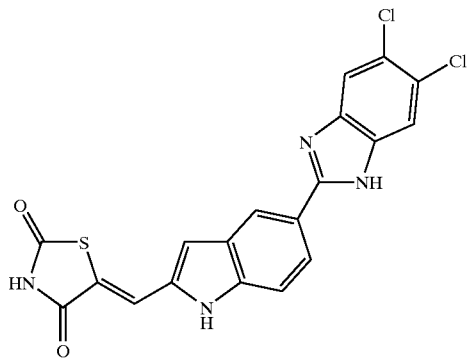

A mixture of 5-dimethoxymethyl-1-(4-methylphenyl)sulfonylindole-2-carboxaldehyde obtained in Example 45 (200 mg, 0.536 mmol), 2,4-thiazolidinedione (75 mg, 0.643 mmol), and piperidine (0.064 mL, 0.64 mmol) in ethanol (6 mL) was heated to reflux for 6 h. Hydrochloric acid (1 mol/L; 1 mL) was added to the mixture, and the precipitated products were collected by filtration followed by washing with ether to afford 5-formyl-1-(4-methylphenyl)sulfonylindol-2-ylmethylene-2,4-thiazolidinedione (155 mg, 68%).

¹H NMR (400 MHz, DMSO-d₆) δ (ppm) 2.25 (s, 3H), 7.32 (s, 1H), 7.32 (d, J=8.2 Hz, 2H), 7.63 (d, J=8.2 Hz, 2H), 7.93 (d, J=9.0 Hz, 1H), 8.24 (s, 1H), 8.27 (s, 1H), 8.27 (s, 1H), 8.28 (d, J=9.0 Hz, 1H), 9.98 (s, 1H), 12.8 (br s, 1H); ESI–MS m/z 425 (M–H)⁻, $C_{20}H_{14}N_2O_5S_2$=426.

General Procedure 2 was then followed to obtain 5,6-dichloro-2-[2-[(2,4-dioxothiazolidin-5-ylidene)methyl]-1-(4-methylphenyl)sulfonylindol-5-yl]benzimidazole.

¹H NMR (400 MHz, DMSO-d₆) δ (ppm) 2.24 (s, 3H), 7.24 (s, 1H), 7.32 (d, J=8.2 Hz, 2H), 7.64 (d, J=8.2 Hz, 2H), 7.80 (br s, 2H), 8.20 (dd, J=9.0, 1.6 Hz, 1H), 8.26 (d, J=9.0 Hz, 1H), 8.28 (s, 1H), 8.42 (s, 1H), 12.8 (br s, 1H), 13.3 (br s, 1H); ESI–MS m/z 583, 581 (M–H)⁻, $C_{26}H_{16}{}^{35}Cl_2N_4O_4S_2$=582.

To a suspension of 5,6-dichloro-2-[2-[(2,4-dioxothiazolidin-5-ylidene)methyl]-1-(4-methylphenyl)sulfonylindol-5-yl]benzimidazole (100 mg, 0.172 mmol) in methanol (7.5 mL) was added aqueous sodium hydroxide (2 mol/L; 1.5 mL), and the mixture was heated to reflux for 3.5 h. The reaction mixture was cooled on an ice bath, and pH was adjusted to 7. The precipitated products were collected by filtration, washed with water, and dried. To a solution of the product (50 mg) in dimethylformamide (2 mL) was added 1,1'-carbonyldiimidazole (15 mg, 0.12 mmol), and the mixture was stirred at room temperature for 30 min. Hydrochloric acid (1 mol/L; 0.5 mL) and water were added to the mixture, and the precipitated product was filtered off and washed with water and ethanol to afford 5,6-dichloro-2-[2-[(2,4-dioxothiazolidin-5-ylidene)methyl]indol-5-yl]benzimidazole (18 mg, 24%).

¹H NMR (400 MHz, DMSO-d₆) δ (ppm) 7.36 (s, 1H), 7.89 (br s, 1H), 8.10 (s, 1H), 8.23 (dd, J=9.0, 1.6 Hz, 1H), 8.35 (br s, 1H), 8.54 (s, 1H), 8.57 (d, J=8.6 Hz, 1H); ESI–MS m/z 429, 427 (M–H)⁻, $C_{19}H_{10}{}^{35}Cl_2N_4O_2S$=428.

Example 47

Preparation of 5,6-Dichloro-2-[5-[(2,4-dioxothiazolidin-5-ylidene)methyl]indol-2-yl]-(methoxymethyl)benzimidazole

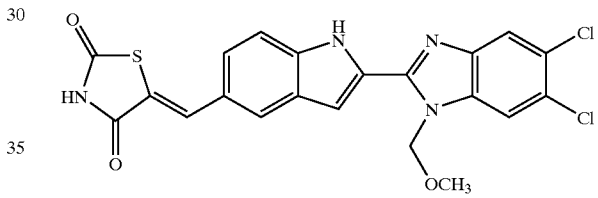

To a solution of 5,6-dichloro-2-[5-formyl-1-(4-methylphenyl)sulfonylindol-2-yl]benzimidazole obtained in Example 45 (824 mg, 1.71 mmol) in dimethylformamide (10 mL) were added diisopropylethylamine (0.59 mL, 3.4 mmol) and chloromethyl methyl ether (0.16 mL, 2.1 mmol), and the mixture was stirred at room temperature for 15 h. Water was added, and the mixture was extracted with ethyl acetate. The organic layer was washed with water and brine, dried on anhydrous sodium sulfate. The solvent was removed under reduced pressure. To the residue were added methanol (80 mL) and 2 mol/L sodium hydroxide (5 mL), and the mixture was heated to reflux for 1 h. Water was added, and the mixture was extracted with ethyl acetate. The organic layer was washed with water and brine, dried on anhydrous sodium sulfate. The solvent was removed under reduced pressure, and the residue was triturated with ether to afford 5,6-dichloro-2-[5-formylindol-2-yl]-1-(methoxymethyl)benzimidazole (570 mg, 89%).

¹H NMR (400 MHz, DMSO-d₆) δ (ppm) 3.36 (s, 3H), 5.81 (s, 2H), 7.41 (d, J=0.8 Hz, 1H), 7.58 (d, J=8.6 Hz, 1H), 7.71 (dd, J=8.6 Hz, 1H), 7.96 (s, 1H), 8.28 (s, 1H), 8.29 (s, 1H), 9.94 (s, 1H), 12.6 (br s, 1H).

General Procedure 1 was then followed to obtain 5,6-dichloro-2-[5-[(2,4-dioxothiazolidin-5-ylidene)methyl]indol-2-yl]-1-(methoxymethyl)benzimidazole.

¹H NMR (400 MHz, DMSO-d₆) δ (ppm) 3.30 (s, 3H), 5.82 (s, 2H), 7.35 (s, 1H), 7.44 (d, J=8.9 Hz, 1H), 7.58 (d, J=8.2 Hz, 1H), 7.87 (s, 1H), 7.97 (d, J=1.2 Hz, 1H), 8.16 (s, 1H), 8.29 (s, 1H), 12.4 (br s, 1H), 12.5 (br s, 1H); ESI–MS m/z 473, 471 (M–H)⁻, $C_{21}H_{14}{}^{35}Cl_2N_4O_3S$=472.

Example 48

Preparation of 5,6-Dichloro-2-[5-[(2,4-dioxothiazolidin-5-ylidene)methyl]-1-methylindol-2-yl]-1-(methoxymethyl)benzimidazole

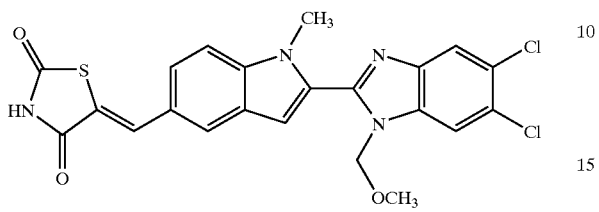

To a solution of 5,6-dichloro-2-[5-formylindol-2-yl]-1-(methoxymethyl)benzimidazole obtained in Example 47 (32 mg, 0.086 mmol) in dimethylformamide (2 mL) were added iodomethane (0.027 mL, 0.43 mmol) and potassium tert-butoxide (19 mg, 0.17 mmol) under nitrogen atmosphere, and the mixture was stirred at room temperature for 18 h. Water was added, and the mixture was extracted with ethyl acetate. The organic layer was washed with water and brine, dried on anhydrous sodium sulfate. The solvent was removed under reduced pressure to afford 5,6-dichloro-2-[5-formyl-1-methylindol-2-yl]-1-methoxymethylbenzimidazole (30 mg, 90%).

¹H NMR (400 MHz, CDCl₃) δ (ppm) 3.45 (s, 3H), 4.08 (s, 3H), 5.52 (s, 2H), 7.50 (d, J=8.6 Hz, 1H), 7.66 (s, 1H), 7.89 (dd, J=8.6, 1.6 Hz, 1H), 7.92 (s, 1H), 8.21 (d, J=0.8 Hz, 1H), 10.0 (s, 1H).

General Procedure 1 was then followed to obtain 5,6-dichloro-2-[5-[(2,4-dioxothiazolidin-5-ylidene)methyl]-1-methylindol-2-yl]-1-methoxymethylbenzimidazole.

¹H NMR (400 MHz, DMSO-d₆) δ(ppm) 3.33 (s, 3H), 4.00 (s, 3H), 5.65 (s, 2H), 7.30 (s, 1H), 7.52 (d, J=8.6 Hz, 1H), 7.74 (d, J=9.0 Hz, 1H), 7.90 (s, 1H), 7.98 (s, 1H), 8.07 (s, 1H), 8.26 (s, 1H), 12.5 (br s, 1H); ESI–MS m/z 487, 485 (M–H)⁻, $C_{22}H_{16}{}^{35}Cl_2N_4O_3S$=486.

Example 49

Preparation of 5,6-Dichloro-2-[5-[(2,4-dioxothiazolidin-5-ylidene)methyl]-1-methylindol-2-yl]benzimidazole

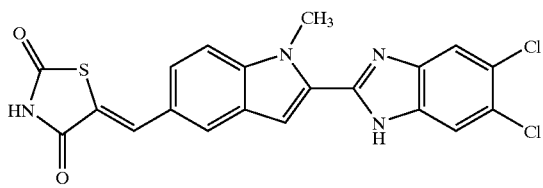

To a solution of 5,6-dichloro-2-[5-[(2,4-dioxothiazolidin-5-ylidene)methyl]-1-methylindol-2-yl]-1-(methoxymethyl)benzimidazole obtained in Example 48 (26 mg, 0.053 mmol) in 1,4-dioxane (5 mL) was added concentrated hydrochloric acid (0.5 mL), and the mixture was heated to reflux for 1 h. The pH was adjusted to 7 by 2 mol/L sodium hydroxide and the precipitated products were collected by filtration to afford 5,6-dichloro-2-[5-[(2,4-dioxothiazolidin-5-ylidene)methyl]-1-methylindol-2-yl]benzimidazole (12 mg, 51%).

¹H NMR (400 MHz, DMSO-d₆) δ (ppm) 4.26 (s, 3H), 7.39 (s, 1H), 7.47 (dd, J=8.6, 1.6 Hz, 1H), 7.71 (d, J=8.6 Hz, 1H), 7.74 (br s, 1H), 7.88 (s, 1H), 7.94 (s, 1H), 7.95 (br s, 1H), 12.5 (br s, 1H), 13.4 (br s, 1H); ESI–MS m/z 443, 441 (M–H)⁻, $C_{20}H_{12}{}^{35}Cl_2N_4O_2S$=442.

Example 50

Preparation of 5,6-Dichloro-2-[1-butyl-5-[(2,4-dioxothiazolidin-5-ylidene)methyl]indol-2-yl]-1-(methoxymethyl)benzimidazole

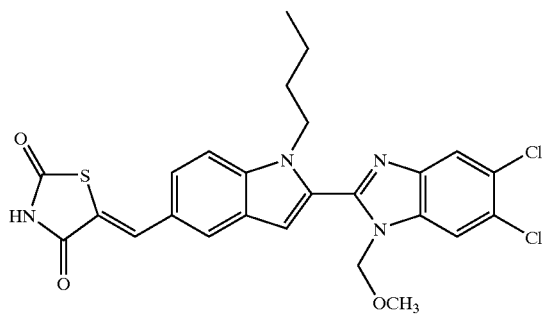

5,6-dichloro-2-[1-butyl-5-[(2,4-dioxothiazolidin-5-ylidene)methyl]indol-2-yl]-1-(methoxymethyl)benzimidazole was prepared from 5,6-dichloro-2-[5-formylindol-2-yl]-1-(methoxymethyl)benzimidazole obtained in Example 47 and 1-iodobutane in a similar manner to Example 48.

ESI–MS m/z 529, 527 (M–H)⁻ $C_{25}H_{22}Cl_2N_4O_3S$=528.

Example 51

Preparation of 5,6-Dichloro-2-[1-butyl-5-[(2,4-dioxothiazolidin-5-ylidene)methyl]indol-2-yl]benzimidazole

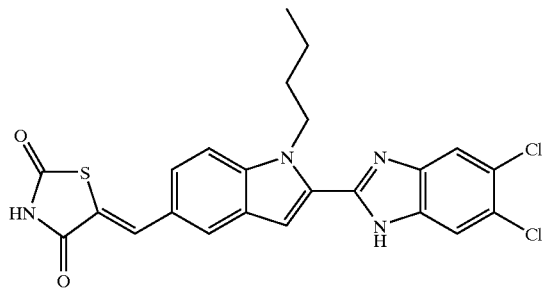

5,6-dichloro-2-[1-butyl-5-[(2,4-dioxothiazolidin-5-ylidene)methyl]indol-2-yl]benzimidazole was prepared in a similar manner to Example 49.

ESI–MS m/z 485, 483 (M–H)⁻, $C_{23}H_{18}{}^{35}Cl_2N_4O_2S$=484.

Example 52

Preparation of 5,6-Dichloro-2-[1-[2-(dimethylamino)ethyl]-5-[(2,4-dioxothiazolidin-5-ylidene)methyl]indol-2-yl]-1-(methoxymethyl)benzimidazole

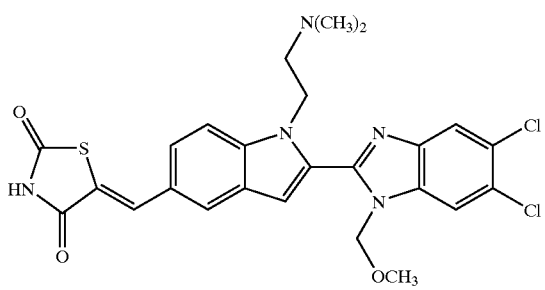

5,6-dichloro-2-[1-[2-(dimethylamino)ethyl]-5-[(2,4-dioxothiazolidin-5-ylidene)methyl]indol-2-yl]-1-(methoxymethyl)benzimidazole was prepared from 5,6-dichloro- 2-[5-formylindol-2-yl]-1-(methoxymethyl)benzimidazole obtained in Example 47 and 2-(dimethylamino)ethyl chloride hydrochloride in a similar manner to Example 48.

ESI-MS m/z 544, 542 (M-H)$^-$ C$_{25}$H$_{22}$$^{35}$Cl$_2$N$_5$O$_3$S=543.

Example 53

Preparation of 5,6-Dichloro-2-[1-[2-(dimethylamino)ethyl]-5-[(2,4-dioxothiazolidin-5-ylidene)methyl]indol-2-yl]benzimidazole

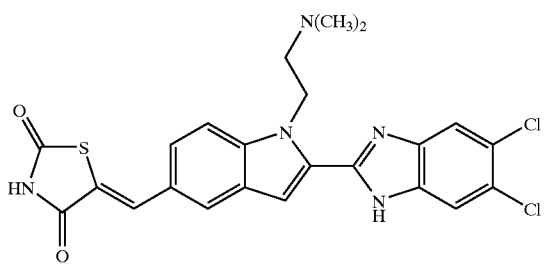

5,6-dichloro-2-[1-[2-(dimethylamino)ethyl]-5-[(2,4-dioxothiazolidin-5-ylidene)methyl]indol-2-yl]benzimidazole was prepared in a similar manner to Example 49.

ESI-MS m/z 500, 498 (M-H)$^-$, C$_{23}$H$_{19}$$^{35}$Cl$_2$N$_5$O$_2$S=499.

Example 54

Preparation of 5,6-Dichloro-1-[[4-(2,4-dioxothiazolidin-5-ylidene)methyl]phenyl]benzimidazole

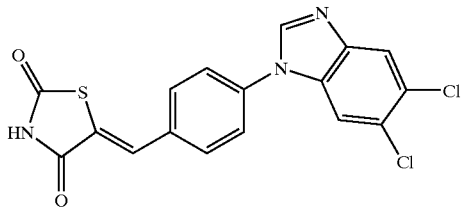

A mixture of 5,6-dichlorobenzimidazole (94 mg, 0.50 mmol), 4-fluorobenzaldehyde (0.064 mL, 0.60 mmol), and potassium carbonate (83 mg, 0.60 mmol) in dimethylsulfoxide (3 mL) was heated at 100° C. for 3 h. The mixture was cooled to room temperature, and water was added. The precipitated product was collected by filtration and washed with water and ethanol to afford 5,6-dicloro-1-(4-formylphenyl)benzimidazole (90 mg, 62%).

$^1$H NMR (400 MHz, DMSO-d$_6$) δ (ppm) 7.94 (d, J=8.6 Hz, 2H), 7.97 (s, 1H), 8.08 (s,1H), 8.11 (d, J=8.6 Hz, 2H), 8.80 (s, 1H), 10.1 (s, 1H).

General Procedure 1 was then followed to obtain 5,6-dichloro-1-[[4-(2,4-dioxothiazolidin-5-ylidene)methyl]phenyl]benzimidazole.

$^1$H NMR (400 MHz, DMSO-d$_6$) δ (ppm) 7.80 (d, J=8.6 Hz, 2H), 7.85 (d, J=8.6 Hz, 2H), 7.87 (s, 1H), 7.95 (s, 1H), 8.07 (s, 1H), 8.75 (s, 1H), 12.7 (br s, 1H); ESI-MS m/z 390, 388 (M-H)$^-$, C$_{17}$H$_9$$^{35}$Cl$_2$N$_3$O$_2$S=389.

Example 55

Preparation of 5,6-Dichloro-1-[[4-(2,4-dioxothiazolidin-5-ylidene)methyl]phenyl]-2-methylbenzimidazole

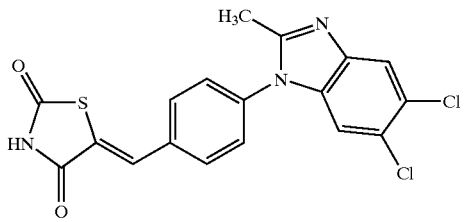

5,6-dichloro-1-[[4-(2,4-dioxothiazolidin-5-ylidene)methyl]phenyl]-2-methylbenzimidazole was obtained from 5,6-dichloro-2-methylbenzimidazole and 4-fluorobenzaldehyde in 2 steps in a similar manner to Example 54.

ESI-MS m/z 404, 402 (M-H)$^-$, C$_{18}$H$_{11}$$^{35}$Cl$_2$N$_3$O$_2$S=403.

Example 56

Preparation of 5,6-Dichloro-1-[[4-(2,4-dioxothiazolidin-5-ylidene)methyl]phenyl]-2-(methythio)benzimidazole

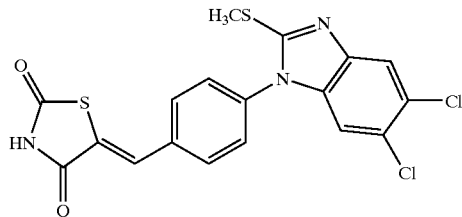

5,6-dichloro-1-[[4-(2,4-dioxothiazolidin-5-ylidene)methyl]phenyl]-2-(methylthio)benzimidazole was obtained from 5,6-dichloro-2-(methylthio)benzimidazole and 4-fluorobenzaldehyde in 2 steps in a similar manner to Example 54.

ESI-MS m/z 436, 434 (M−H)⁻, $C_{18}H_{11}{}^{35}Cl_2N_3O_2S_2=$ 435.

Example 57

Preparation of Affinity Purified Extract

Extracts used for screening telomerase inhibitors were routinely prepared from 293 cells over-expressing the protein catalytic subunit of telomerase (hTERT). These cells were found to have 2–5 fold more telomerase activity than parental 293 cells. 200 ml of packed cells (harvested from about 100 liters of culture) were resuspended in an equal volume of hypotonic buffer (10 mM Hepes pH 7.9, 1 mM $MgCl_2$, 1 mM DTT, 20 mM KCl, 1 mM PMSF) and lysed using a dounce homogenizer. The glycerol concentration was adjusted to 10% and NaCl was slowly added to give a final concentration of 0.3 M. The lysed cells were stirred for 30 min and then pelleted at 100,000×g for 1 hr. Solid ammonium sulfate was added to the S100 supernatant to reach 42% saturation. The material was centrifuged; the pellet was resuspended in one fifth of the original volume and dialyzed against Buffer 'A' containing 50 mM NaCl. After dialysis the extract was centrifuged for 30 min at 25,000×g. Prior to affinity chromatography, Triton X-100 (0.5%), KCl (0.3 M) and tRNA (50 µg/ml) were added. Affinity oligo (5' biotinTEG-biotinTEG-biotinTEG-GTA GAC CTG TTA CCA guu agg guu ag 3'; lower case represents 2' O-methyl ribonucleotides and upper case represents deoxynucleotides) was added to the extract (1 nmol per 10 ml of extract). After an incubation of 10 min at 30° C., Neutravidin beads (Pierce; 250 µl of a 50% suspension) were added and the mixture was rotated overnight at 4° C. The beads were pelleted and washed three times with Buffer 'B' containing 0.3 M KCl, twice with Buffer 'B' containing 0.6 M KCl, and twice more with Buffer B containing 0.3 M KCl. Telomerase was eluted in Buffer 'B' containing 0.3 M KCl, 0.15% Triton X-100 and a 2.5 molar excess of displacement oligo (5'-CTA ACC CTA ACT GGT AAC AGG TCT AC-3' at 0.5 ml per 125 µl of packed Neutravidin beads) for 30 min. at room temperature. A second elution was performed and pooled with the first. Purified extracts typically had specific activities of 10 fmol nucleotides incorporated/min/µl extract, or 200 nucleotides/min/mg total protein.

| Buffer 'A' | Buffer 'B' |
|---|---|
| 20 mM Hepes pH 7.9 | 20 mM Hepes pH 7.9 |
| 1 mM MgCl2 | 1 mM EDTA |
| 1 mM DTT | 1 mM DTT |
| 1 mM EGTA | 10% glycerol |
| 10% glycerol | 0.5 Triton |

Example 58

Telomerase Specific Activity Determination

Three separate 100 µl telomerase assays are set up with the following buffer solutions: 50 mM Tris acetate, pH 8.2, 1 mM DTT, 1 mM EGTA, 1 mM $MgCl_2$, 100 mM K acetate, 500 µM dATP, 500 µM TTP, 10 µM $^{32}P$-dGTP (25 Ci/mmol), and a00 nM d(TTAGGG)$_3$. To the individual reactions 2.5, 5 or 10 µl of affinity-purified telomerase (see Example 57) is added and the reactions are incubated at 37° C. At 45 and 90 minutes, 40 µl aliquots are removed from each reaction and added to 160 µl of Stop Buffer (100 mM NaCl, 10 mM Na pyrophosphate, 0.2% SDS, 2 mM EDTA, 100 µg/ml tRNA). 10 µl trichloroacetic acid (TCA) (100%) is added and the sample is incubated on ice for 30 minutes. The sample is pelleted in a microcentrifuge (12000×g force) for 15 minutes. The pellet is washed with 1 ml 95% ethanol and pelleted again in the microcentrifige (12000×g force) for 5 minutes. The pellet is resuspended in 50 µl $dH_2O$ and transferred to a 12×75 glass test tube containing 2.5 ml of ice cold solution of 5% TCA and 10 mM Na pyrophosphate. The sample is incubated on ice for 30 minutes. The sample is filtered through a 2.5 cm wet ($dH_2O$) GFC membrane (S&S) on a vaccum filtration manifold. The filter is washed three times under vacuum with 5 ml ice cold 1% TCA, and once with 5 ml 95% ethanol. The filter is dried and counted in a scintillation counter using scintillation fluid. The fmol of nucleotide incorporated is determined from the specific activity of radioactive tracer. The activity of extract is calculated based on the dNTP incorporated and is expressed as fmol dNTP/min/µl extract.

Example 59

Telomerase Activity Assay

Bio-Tel FlashPlate Assay

An assay is provided for the detection and/or measurement of telomerase activity by measuring the addition of TTAGGG telomeric repeats to a biotinylated telomerase substrate primer; a reaction catalyzed by telomerase. The biotinylated products are captured in streptavidin-coated microtiter plates. An oligonucleotide probe complementary to 3.5 telomere repeats labeled with [$^{33}P$] is used for measuring telomerase products, as described below. Unbound probe is removed by washing and the amount of probe annealing to the captured telomerase products is determined by scintillation counting.

Method:

1. Compounds are stored as concentrated stocks and dissolved in 100% dimethylsulfoxide (DMSO).

2. For testing, the compounds are diluted to a 15×working stock in 50% DMSO and 2 µl is dispensed into two wells of a 96-well microtiter dish (assayed in duplicate).

3. Telomerase extract is diluted to a specific activity of 0.04–0.09 fmol dNTP incorporated/min./µl in Telomerase Dilution Buffer and 18 µl added to each sample well to preincubate with compound for 30 minutes at room temperature.

4. The telomerase reaction is initiated by addition of 10 μl Master Mix to the wells containing telomerase extract and compound. The plates are sealed and incubated at 37° C. for 90 min.

5. The reaction is stopped by the addition of 10 μl HCS.

6. 25 μl of the reaction mixture is transferred to a 96-well streptavidin-coated FlashPlate (NEN) and incubated for 2 hours at room temperature with mild agitation.

7. The wells are washed three times with 180 μl 2×SSC without any incubation.

8. The counts of probe annealed to biotinylated telomerase products are detected on a scintillation counter.

Buffers:
Telomerase Dilution Buffer
  50 mM Tris-acetate, pH 8.2
  1 mM DTT
  1 mM EGTA
  1 mM $MgCl_2$
  830 nM BSA
Master Mix (MM)
  50 mM Tris-acetate, pH 8.2
  1 mM DTT
  1 mM EGTA
  1 mM $MgCl_2$
  150 mM K acetate
  10 μM dATP
  20 μM dGTP
  120 μM dTTP
  100 nM biotinylated primer (5'-biotin-AATCCGTCGAGCAGAGTT-3')
  5.4 nM labeled probe [5'-CCCTAACCCTAACCCTAACCC-($^{33}$P) $A_{1-50}$-3']; specific activity approximately $10^9$ cpm/μg or higher
Hybridization Capture Solution (HCS)
  12×SSC (1×=150 mM NaCl/30 mM $Na_3$Citrate)
  40 mM EDTA
  40 mM Tris-HCl, pH 7.0

Using the foregoing assay, the compounds of Examples 1–56 were shown to have telomerase $IC_{50}$ values below 100 μM.

Example 60

Anti-tumor Activity

Ex vivo Studies a. Reduction of Telomere Length in Tumor Cells

Colonies of the tumor cell lines, such as the ovarian tumor cell lines OVCAR-5 and SK-OV-3, and normal human cells used as a control (e.g., normal human BJ cells) are prepared using standard methods and materials. In one test, the colonies are prepared by seeding 15-centimeter dishes with about $10^6$ cells in each dish. The dishes are incubated to allow the cell colonies to grow to about 80% confluence, at which time each of the colonies are divided into two groups. One group is exposed to a subacute dose of a compound of the invention at a predetermined concentration (e.g., between about 5 μM and about 20 μM) for a period of about 4–8 hours after plating following the split; the other group is exposed to a control (e.g., DMSO).

Each group is then allowed to continue to divide, and the groups are split evenly again (near confluence). The same number of cells are seeded for continued growth. The compound or control is added every fourth day to the samples at the same concentration delivered initially. Remaining cells are analyzed for telomere length. As the untested cell cultures near confluence, the samples are split again as just described. This sequence of cell doubling and splitting is continued for about 20 to 25 doublings. Thus, a determination of telomere length as a function of cell doublings is obtained.

Telomere length is determined by digesting the DNA of the cells using restriction enzymes specific for sequences other than the repetitive $T_2 AG_3$ sequence of human telomeres (TRF analysis). The digested DNA is separated by size using standard techniques of gel electrophoresis to determine the lengths of the telomeric repeats, which appear, after probing with a telomere DNA probe, on the gel as a smear of high-molecular weight DNA (approximately 2 Kb-15 Kb).

The results of the telomere length analysis are expected to indicate that the compounds of the invention have no affect on the rate of decrease in telomere length for control cells as a function of progressive cell doublings. With respect to the tumor cell lines, however, measurable decreases in telomere length are expected to be determined for tumor cells exposed to the compounds of the invention. Tumor cells exposed to the control are expected to maintain steady telomere lengths. Thus, the compounds of the invention are expected to cause resumption of the normal loss of telomere length as a function of cell division in tumor cells.

In another experiment, HEK-293 cells are incubated with a compound of the invention and a control at concentrations between about 1 μM and about 20 μM using the protocol just described. Cells are expected to enter crisis (i.e., the cessation of cell function) within several weeks following administration of the test compound of the invention. In addition, TRF analysis of the cells using standard methodology is expected to show that the test compounds of the invention are effective in reducing telomere length. In addition to the HEK-293 cells described above, this assay can be performed with any telomerase-positive cell line, such as HeLa cells.

b. Specificity

Compounds of the invention are screened for activity ($IC_{50}$) against telomerase and several enzymes having nucleic acid binding or modifying activities related to telomerase using standard techniques. The enzymes being screened include Telomerase, DNA Polymerase I, HeLa RNA Polymerase II, T3 RNA Polymerase, MMLV Reverse Transcriptase, Topoisomerase I, Topoisomerase II, Terminal Transferase and Single-Stranded DNA Binding Protein (SSB). The specificity of a compound of the invention for telomerase is determined by comparing the $IC_{50}$ of the compound with respect to telomerase with the $IC_{50}$ values of the compound for each of the enzymes being screened. The compound is determined to have high specificity for telomerase if the $IC_{50}$ for telomerase of the compound is lower than the $IC_{50}$ vaules for each of the enzymes being screened.

Alternatively, telomerase inhibitory activity of the compounds was measured in accordance with a known method (U.S. Pat. No. 5,760,062). That is, a dimethyl sulfoxide (DMSO) solution of each agent was mixed with partially purified telomerase from a nuclear extract of HEK293 cells and incubated in the presence of an oligodeoxynucleotide to be used as the substrate and deoxynucleotide triphosphate. The obtained reacted product (DNA having a telomere sequence) was adsorbed on a membrane, and hybridization was carried out using a labeled oligonucleotide probe having a sequence complementary to the telomere sequence. The inhibition ratio was calculated based on the ratio of the signal of label on the membrane in the presence of the agent to the signal of label in the absence of the agent (control).

Also, concentration of each agent which inhibits 50% of the enzyme activity based on the control was used as $IC_{50}$. Results of the measurement of inhibition activity of selected compounds are shown in Table 1.

TABLE 1

In vitro telomerase inhibition activity

| Compound of Example | $IC_{50}$ ($\mu$M) |
|---|---|
| 1 | 1.86, 1.1, 1.22, 0.85, 1.14 |
| 2 | 1.05, 1.52 |
| 3 | 5.44, 6.2 |
| 4 | 4.3, 3.69 |
| 5 | 4.98, 2.95 |
| 6 | 3.04, 3.35 |
| 14 | 1.61, 1.92 |
| 15 | 3.01, 2.43 |
| 20 | 2.28, 3.26 |
| 21 | 19.2, 15.92 |
| 28 | 14.48, 14.95 |
| 29 | 1.89, 2.26 |
| 30 | 5.19, 2.76 |
| 32 | 1.96, 1.91 |
| 33 | 3.18, 2.47 |
| 39 | 0.44, 0.92, 1.01 |
| 40 | 0.29, 0.55, 0.51 |
| 45 | 0.61 |
| 46 | 5.4 | c. Cytotoxicity

The XTT assay for cytotoxicity is performed using HeLa cells. The cell lines used in the assay are exposed to a compound of the invention for 72 hours at concentrations ranging from about 1 $\mu$M to about 1,000 $\mu$M. During this period, the optical density (OD) of the samples is determined for light at 540 nonometers (nm). No significant cytotoxic effects are expected to be observed at concentrations less than about 5 $\mu$M. It will be appreciated that other tumor cells lines such as the ovarian tumor cell lines OVCAR-5 and SK-OV-3 can be used to determine cytotoxicity in addition to control cell lines such as normal human BJ cells. Other assays for cytotoxicity such as the MTT assay (see Berridge et al., 1996, Biochemica 4:14–19) and the alamarBlue™ assay (U.S. Pat. No. 5,501,959) can be used as well.

Some compounds may induce G2 arrest at concentrations above about 5 $\mu$M (i.e., at 10 $\mu$M–20 $\mu$M concentrations or higher). Preferably, to observe any telomerase inhibiting effects the compounds should be administered at a concentration below the level of cytotoxicity. Nevertheless, since the effectiveness of many cancer chemotherapeutics derives from their cytotoxic effects, it is within the scope of the present invention that the compounds of the present invention be administered at any dose for which chemotherapeutic effects are observed.

In vivo Studies

A human tumor xenograft model in which OVCAR-5 tumor cells are grafted into nude mice can be constructed using standard techniques and materials. The mice are divided into two groups. One group is treated intraperitoneally with a compound of the invention. The other group is treated with a control comprising a mixture of either DMSO or ethanol and emulphor (oil) and phosphate buffer solution (PBS). The average tumor mass for mice in each group is determined periodically following the xenograft using standard methods and materials.

In the group treated with a compound of the invention, the average tumor mass is expected to increase following the initial treatment for a period of time, after which time the tumor mass is expected to stabilize and then begin to decline. Tumor masses in the control group are expected to increase throughout the study. Thus, the compounds of the invention are expected to lessen dramatically the rate of tumor growth and ultimately induce reduction in tumor size and elimination of the tumor.

In another experiment, each agent is allowed to contact with human renal carcinoma cell line ACHN for 3 days, and then a cell extract is prepared by a known method (U.S. Pat. No. 5,629,154) to measure the enzyme activity. That is, a cell extract is prepared using a buffer solution containing 0.5% CHAPS. Using the extract, TRAP (Telomeric Repeat Amplification Protocol) assay is carried out in vitro ($TRAP_{EZE}$™ ELISA Telomerase Detection Kit, manufactured by Intergen). The ratio (%) of the enzyme activity in the extract from agent-treated cells to the enzyme activity in the extract from agent-untreated cells is calculated.

Thus, the present invention provides novel compounds, compositions and methods for inhibiting telomerase activity and treating disease states in which telomerase activity has deleterious effects, especially cancer. The compounds of the invention provide a highly selective and effective treatment for malignant cells that require telomerase activity to remain immortal; yet, without affecting non-malignant cells.

While the preferred embodiment of the invention has been illustrated and described, it will be appreciated that various changes can be made therein without departing from the spirit and scope of the invention.

We claim:

1. A method of inhibiting a telomerase enzyme comprising contacting the telomerase enzyme with a compound having the following structure:

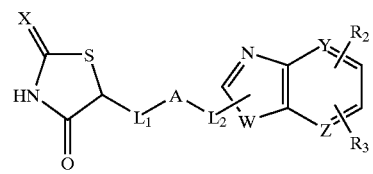

wherein X is O or S;

$L_1$ is a direct bond, —$CHR_1$—, or =$CR_1$—, wherein $R_1$ is H or alkyl;

A is aryl or heteroaryl;

$L_2$ is a direct single bond or a linking group having from 1 to 3 atoms independently selected from unsubstituted or substituted carbon, N, O or S;

W is selected from the group consisting of O, $NR_5$, and S, wherein $R_5$ is selected from the group consisting of H, alkyl, aryl, and aralkyl;

Y and Z are independently selected to be C or N; and $R_2$, and $R_3$ are independently selected from the group consisting of hydrogen, hydroxyl, halogen, alkyl, aryl, alkoxyl, cyano, nitro, alkylthio, arylthio, aralkyl, and heteroaryl;

or a pharmaceutically acceptable salt thereof.

2. The method of claim 1, wherein X is O.

3. The method of claim 2, wherein $L_1$ is a direct bond.

4. The method of claim 2, wherein $R_1$ is H.

5. The method of claim 2, wherein A is selected from the group consisting of aryl, substituted or unsubstituted pyridine, substituted or unsubstituted thiophene, substituted or unsubstituted furan, substituted or unsubstituted naphthalene, substituted or unsubstituted quinoline, and substituted or unsubstituted indole.

6. The method of claim 5, wherein A is selected from the group consisting of phenyl, naphthalene, pyridine, indole, quinoline, furan, or thiophene.

7. The method of claim 2, wherein W is $NR_5$.

8. The method of claim 7, wherein $R_2$ and $R_3$ are halogen.

9. The method of claim 8, wherein at least one of $R_2$, $R_3$, or $R_5$ is:

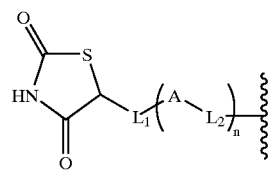

wherein n is 0 or 1.

10. A method of inhibiting a telomerase enzyme comprising contacting the telomerase enzyme with a compound having the following structure:

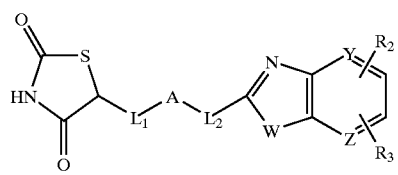

wherein $L_1$ is a direct bond, —$CHR_1$—, or =$CR_1$—, wherein $R_1$ is H or alkyl;

A is aryl or heteroaryl;

$L_2$ is a direct single bond or a linking group having from 1 to 3 atoms independently selected from unsubstituted or substituted carbon, N, O or S;

W is selected from the group selected from O, $NR_5$, and S, wherein $R_5$ is selected from the group consisting of H, alkyl, aryl, and aralkyl;

Y and Z are independently selected to be C or N; and $R_2$ and $R_3$ are independently selected from the group consisting of hydrogen, hydroxyl, halogen, alkyl, aryl, alkoxyl, cyano, nitro, alkylthio, arylthio, aralkyl, and heteroaryl;

or a pharmaceutically acceptable salt thereof.

11. The method of claim 10, wherein W is $NR_5$.

12. The method of claim 11, wherein $R_5$ is selected from the group consisting of methyl, ethyl, propyl, butyl, allyl, ethoxycarbonylmethyl, and 2-(dimethylamino)ethyl.

13. The method of claim 11, wherein $R_5$ is selected from the group consisting of benzyl, 3,4-dichlorobenyzl, 4-formylbenzyl, 4-methoxycarbonylbenzyl, 2-naphtylmethyl, and 5-chlorothiophen-2-ylmethyl.

14. The method of claim 10, wherein at least one of $R_2$, $R_3$, or $R_5$ is:

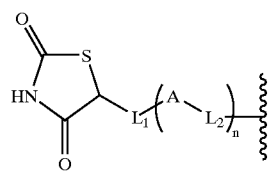

wherein n is 0 or 1.

15. The method of claim 10, wherein $L_1$ is =CH—, $L_2$ is a direct bond, W is S, Y is CH, and Z is CH.

16. A method of inhibiting a telomerase enzyme comprising contacting the telomerase enzyme with a compound having the following structure:

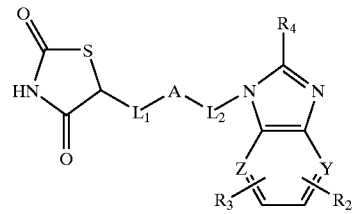

wherein $L_1$ is a direct bond, —$CHR_1$—, or =$CR_1$—, wherein $R_1$ is H or alkyl;

A is aryl or heteroaryl;

$L_2$ is a direct single bond or a linking group having from 1 to 3 atoms independently selected from unsubstituted or substituted carbon, N, O or S;

Y and Z are independently selected to be C or N; and $R_2$, $R_3$ and $R_4$ are independently selected from the group consisting of hydrogen, hydroxyl, halogen, alkyl, aryl, alkoxyl, cyano, nitro, alkylthio, arylthio, aralkyl, and heteroaryl;

or a pharmaceutically acceptable salt thereof.

17. The method of claim 16, wherein $R_4$ is H, methyl, phenyl, or $SCH_3$.

18. The method of claim 16, wherein at least one of $R_2$, $R_3$, or $R_4$ is:

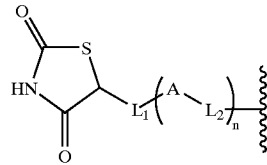

wherein n is 0 or 1.

19. The method of claim 2, wherein A is aryl, $L_1$ and $L_2$ are direct bonds, W is $NR_5$ and $R_2$ and $R_3$ are halogen.

20. The method of claim 19, wherein A is phenyl, pyridine, indole, quinoline, furan, or thiophene.

21. The method of claim 20, wherein $R_5$ is hydrogen, and $R_2$ and $R_3$ are chloride.

* * * * *